US008566038B2

(12) United States Patent (10) Patent No.: US 8,566,038 B2
Gimzewski et al. (45) Date of Patent: Oct. 22, 2013

(54) COMPOSITIONS AND METHODS FOR ANALYZING IMMOBILIZED NUCLEIC ACIDS

(75) Inventors: James K. Gimzewski, Topanga, CA (US); Bhubaneswar Mishra, New York, NY (US); Jason C. Reed, Richmond, VA (US)

(73) Assignees: The Regents of the University of California, Oakland, CA (US); New York University, New York, NY (US)

( * ) Notice: Subject to any disclaimer, the term of this patent is extended or adjusted under 35 U.S.C. 154(b) by 1427 days.

(21) Appl. No.: 11/582,938

(22) Filed: Oct. 17, 2006

(65) Prior Publication Data

US 2007/0092905 A1 Apr. 26, 2007

Related U.S. Application Data

(60) Provisional application No. 60/729,184, filed on Oct. 21, 2005.

(51) Int. Cl.
*G01Q 10/00* (2010.01)
*G01N 33/48* (2006.01)

(52) U.S. Cl.
USPC .......................................... 702/19; 977/881

(58) Field of Classification Search
None
See application file for complete search history.

(56) References Cited

U.S. PATENT DOCUMENTS

| 5,229,606 | A | * | 7/1993 | Elings et al. ................... 850/1 |
| 5,601,982 | A | | 2/1997 | Sargent et al. |
| 6,610,256 | B2 | | 8/2003 | Schwartz |
| 6,716,578 | B1 | | 4/2004 | Henderson et al. |
| 7,507,957 | B2 | * | 3/2009 | Fujihira et al. ................ 250/306 |
| 2004/0248144 | A1 | * | 12/2004 | Mir .................................. 435/6 |

OTHER PUBLICATIONS

Marsh et al. "A new DNA nanostructure, the G-wire, imaged by scanning probe microscopy," (Nucleic Acids Research, vol. 23 (1995) pp. 696-700).*
Fang et al., "Solid-state DNA Sizing by Atomic Force Microscopy," (Anal. Chem, vol. 70 (1998) pp. 2123-2929).*
Allison et al.(1996) "Direct atomic force microscope imaging of EcoRI endonuclease site specifically bound to plasmid DNA molecules" *Proc. Natl. Acad. Sci. USA* 93(17): 8826-8829.
Berge et al. (2000), "Translocation-Independent Dimerization of the EcoKI Endonuclease Visualized by Atomic Force Microscopy" *Biophysical Journal.* 79:479-484.
Britt and Hlady, (1996) "An AFM Study of the Effects of Silanization Temperature, Hydration, and Annealing on the Nucleation and Aggregation of Condensed OTS Domains on Mica", *Journal of Colloid and Interface Science* 178(2): 775-784.
Bunker et al. (2000), The Impact of Solution Agglomeration on the Deposition of Self-Assembled Monlayers, *Langmuir* 16(20): 7742-7751.
Collins et al. (2003) "A vision for the future of genomics research", *Nature* 422(6934): 835-847.
Glaser et al. (2004) "Investigation of the Role of the Interplay between Water and Temperature on the Growth of Alkylsiloxane Submonolayers on Silicon", *Langmuir* 20(13): 5599-5604.

Hansma (2001) "Surface Biology of DNA by Atomic Force Microscopy", *Annual Review of Physical Chemistry* 52: 71-92.
Hori et al. (1998), "The measurement of exonuclease activities by atomic force microscopy" *European Biophysics Journal with Biophysics Letters* 27(1): 63-68.
Hoyt et al. (2000), "Identifying sequence similarities between DNA molecules" *Ultramicroscopy* 82(1-4): 237-244.
Jing et al. (1998). "Automated high resolution optical mapping using arrayed fluid-fixed DNA molecules" Proc. Natl. Acad. Sci. USA 95(14): 8046-8051.
Kim et al. (2004), "Visualizing a Hybridized PNA Probe on a DNA Molecule with Near-Field Optical Microscopy", *Nano Letters* 4(11): 2091-2097.
Lim et al. (2001), "Shotgun Optical Maps of the Whole *Escherichia coli* O157:H7 Genome", *Genome Research* 11(9): 1584-1593.
Nakamura et al. (1999), "Atomic force microscope observation of plasmid deoxyribose nucleic acid with restriction enzyme" *Journal of Vacuum Science & Technology B* 17(2): 288-293.
Potaman et al. (2004). Length-dependent structure formation in Friedreich ataxis $(GAA)_n (TTC)_n$ repeats at neutral pH, *Nucleic Acids Research* 32(3): 1224-1231.
Reed et al. (1998). "A Quantitative Study of Optical Mapping Surfaces by Atomic Force Microscopy and Restriction Endonuclease Digestion Assays", *Analytical Biochemistry* 259(1): 80-88.
Samad et al. (1995). "Mapping the genome one molecule at a time—optical mapping", *Nature* 378(6556): 516-517.
Schwartz (2001). "Mechanics and Kinetics of Self-Assembled Monolayer Formation" *Annual Review of Physical Chemistry* 52: 107-137.
Seong et al. (2000) "Single-Molecular ARM Probing of Apecific DNA Squencing Using RecA-Promoted Homologous Pairing and Strand Exchange", *Analytical Chemistry* 72(6): 1288-1293.
Sun and Yokota (2000). "MutS-Mediated Detection of DNA Mismatches Using Atomic Force Microscopy", *Analytical Chemistry* 72(14): 3138-3141.
Sung et al. (2000), "Reversible Liquid—Liquid Transitions in the Early Stages of Monolayer Self-Assembly" *Journal of Physical Chemistry B* 104(7): 1556-1559.
Woolley et al. (2000). "Direct haplotyping of kilobase-size DNA using carbon nanotube probes", *Nature Biotechnology* 18(7): 760-763.
Zhang and Srinivasan (2004). "Self-Assembled Molecular Films of Aminosilanes and Their Immobilization Capacities", *Langmuir* 20(6): 2309-2314.
Zhou et al. (2002). "A Whole-Genome Shotgun Optical Map of *Yersinia pestis* Strain KIM" *Applied and Environmental Microbiology* 68(12): 6321-6331.
Reed et al., "Single molecule transcription profiling with AFM", *Nanotechnology*, 18(4):44032 (2007).
Schwartz et al., "Ordered Restriction Maps of *Saccharomyces cerevisiae* Chromosomes Constructed by Optical Mapping", *Science*, 262:110-114 (1993).

* cited by examiner

*Primary Examiner* — Anna Skibinsky
(74) *Attorney, Agent, or Firm* — Paula A. Borden; Bozicevic, Field & Francis, LLP.

(57) ABSTRACT

The present invention provides methods of detecting a nucleic acid analyte in a sample. The present invention further provides a method for assigning a profile of a feature to a nucleic acid. The present invention further provides a computer program product for use in a subject method. The present invention further provides a system for detecting a nucleic acid in a sample; and a system for assigning a profile of a feature to a nucleic acid. The present invention further provides a method for immobilizing a nucleic acid onto an insoluble support; and further provides insoluble support having nucleic acid(s) immobilized thereon. The present invention further provides a method of diagnosing a disorder or condition in an individual, where the method involves use of a subject method for detecting a nucleic acid analyte.

14 Claims, 19 Drawing Sheets

◯ = restriction endonuclease    GTAC = nucleotide sequence (a) Sequence

FIG. 6 pOTB7
1,815 bp
5' ~~~~CTGCAG~~~~~~~~~~~~~~~~~~~~~~~~~~~~ 3'
            |
           354
                Pst I

CD44 cDNA
1,775 bp
5' ~~~~CTGCAG~~~~~~~~~~~~~~~~CTGCAG~~~~~ 3'
            |                      |
           354                   1,046
                Pst I               Pst I

FIG. 8A
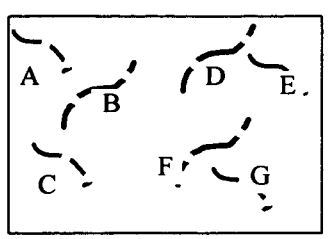
FIG. 8B
A.00010010
B.00010000010
C.00010010
D.00010000010
E.00000010
F.00010000010
G.00000010
FIG. 8C
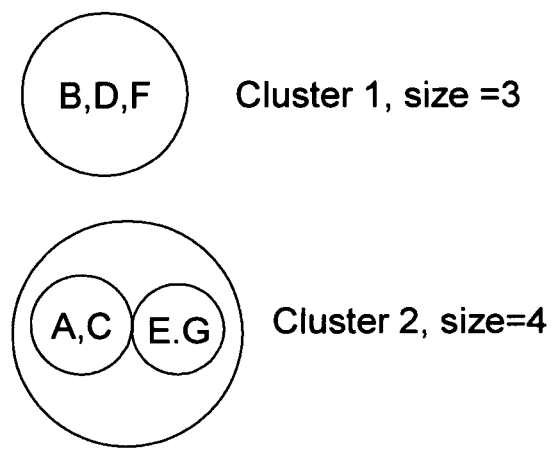
Cluster 1, size =3
Cluster 2, size=4

COMPOSITIONS AND METHODS FOR ANALYZING IMMOBILIZED NUCLEIC ACIDS

CROSS-REFERENCE

This application claims the benefit of U.S. Provisional Patent Application No. 60/729,184, filed Oct. 21, 2005, which application is incorporated herein by reference in its entirety.

STATEMENT REGARDING FEDERALLY SPONSORED RESEARCH

This invention was made with government support under Grant No. 5R21HG3714-2 awarded by the National Institutes of Health. The government has certain rights in the invention.

FIELD OF THE INVENTION

The present invention is in the field of substrates for nucleic acids. The present invention is also in the field of nucleic acid detection and analysis.

BACKGROUND OF THE INVENTION

Gene expression profiles can distinguish normal from diseased cells, making expression profiling a standard approach for identifying potential biochemical pathway abnormalities and therapeutic targets. Improvements in the generation of microarrays, newer multiplex probe hybridization techniques, and advances in data analysis have led to increasingly accurate and reproducible results.

However, expression microarrays remain suboptimal in situations where materials used to make hybridization probes are limited and the detection sensitivity is too low. In such circumstances pooled material from several sources or probe amplification techniques have been used, although pooled samples may still cause difficulty in measuring low abundance RNAs without probe amplification. Polymerase chain reaction (PCR)-based amplification methods are highly sensitive but susceptible to amplification artifacts when used to increase very low abundance species, such as tissue-specific transcription factors. A related technique, linear replication, is more specific but much less sensitive. In practice, gene expression analysis with reverse transcription (RT)-PCR is limited to <$10^2$ distinct RNA species within a sample. An additional limitation to microarray approaches is that they are prone to false positives when samples contain multiple molecules with similar sequences, such as closely related members of gene families or alternatively spliced gene products.

The frontier of gene expression analysis lies where microarrays and amplification-based detection methods together fall short. This includes samples with high tissue complexity, such as in neurologic, immunologic, or malignant tissues; where pooling of material from multiple samples obscures important biological differences; and where regulatory proteins expressed at low abundance exert large biological effects from small changes in expression level. A single cell contains $10^5$-$10^6$ mRNA molecules, while each low abundance species may be present in only a few copies per cell.

There is a need in the art for detection methods that allow for detection of very low abundance mRNA in a sample, without the need for amplification of the mRNA in the sample. The present invention addresses this need.

LITERATURE

U.S. Pat. No. 5,601,982; Reed et al. (1998) *Anal. Biochem.* 259:80-88; Berge et al. (2000) *Biophys. J.* 79:479-484; U.S. Pat. No. 6,716,578; U.S. Pat. No. 6,610,256; Allison et al. (1996) *Proc. Natl. Acad. Sci. USA* 93(17): 8826-8829; Allison et al. (1997) *Genomics* 41(3): 379-384; Britt et al. (1996) *Journal of Colloid and Interface Science* 178(2): 775-784; Bunker et al. (2000) *Langmuir* 16(20): 7742-7751; Collins et al. (2003) *Nature* 422(6934): 835-847; Glaser et al. (2004) *Langmuir* 20(13): 5599-5604; Hansma (2001) *Annual Review of Physical Chemistry* 52: 71-92; Hori et al. (1998). *European Biophysics Journal with Biophysics Letters* 27(1): 63-68; Hoyt, et al. (2000). *Ultramicroscopy* 82(1-4): 237-244; Jing et al. (1998). Proc. Natl. Acad. Sci. USA 95(14): 8046-8051; Kim et al. (2004). *Nano Letters* 4(11): 2091-2097; Lim et al. (2001). *Genome Research* 11(9): 1584-1593; Nakamura et al. (1999). *Journal of Vacuum Science & Technology B* 17(2): 288-293; Potaman et al. (2004). *Nucleic Acids Research* 32(3): 1224-1231; Reed et al. (1998). *Analytical Biochemistry* 259(1): 80-88; Samad et al. (1995). *Nature* 378(6556): 516-517; Schwartz (2001). *Annual Review of Physical Chemistry* 52: 107-137; Seong et al. (2000) *Analytical Chemistry* 72(6): 1288-1293; Sun and Yokota (2000). *Analytical Chemistry* 72(14): 3138-3141; Sung et al. (2000). *Journal of Physical Chemistry B* 104(7): 1556-1559; Woolley et al. (2000). "*Nature Biotechnology* 18(7): 760-763; Zhan and Srinivasan (2004). *Langmuir* 20(6): 2309-2314; Zhou Deng, et al. (2002). *Applied and Environmental Microbiology* 68(12): 6321-6331.

SUMMARY OF THE INVENTION

The present invention provides methods of detecting a nucleic acid analyte in a sample. The methods generally involve modifying immobilized nucleic acids from a sample onto an insoluble support in a substantially elongated configuration, where modification generates an identifying feature that identifies the analyte; and detecting the identifying feature(s) using scanning probe microscopy, to detect the analyte. The present invention further provides a method for assigning a profile of a feature to a nucleic acid. The present invention further provides a computer program product for use in a subject method. The present invention further provides a system for detecting a nucleic acid in a sample; and a system for assigning a profile of a feature to a nucleic acid. The present invention further provides a method for immobilizing a nucleic acid onto an insoluble support; and further provides insoluble support having nucleic acid(s) immobilized thereon. The present invention further provides a method of diagnosing a disorder or condition in an individual, where the method involves use of a subject method for detecting a nucleic acid analyte.

BRIEF DESCRIPTION OF THE DRAWINGS

FIG. 6 depicts schematically the position of PstI recognition site in pOTB7 and CD44 cDNA, and expected size fragments upon digestion with PstI.

FIGS. 8A-C depict a schematic representation of single molecule profiling.

DEFINITIONS

Figure 1A:
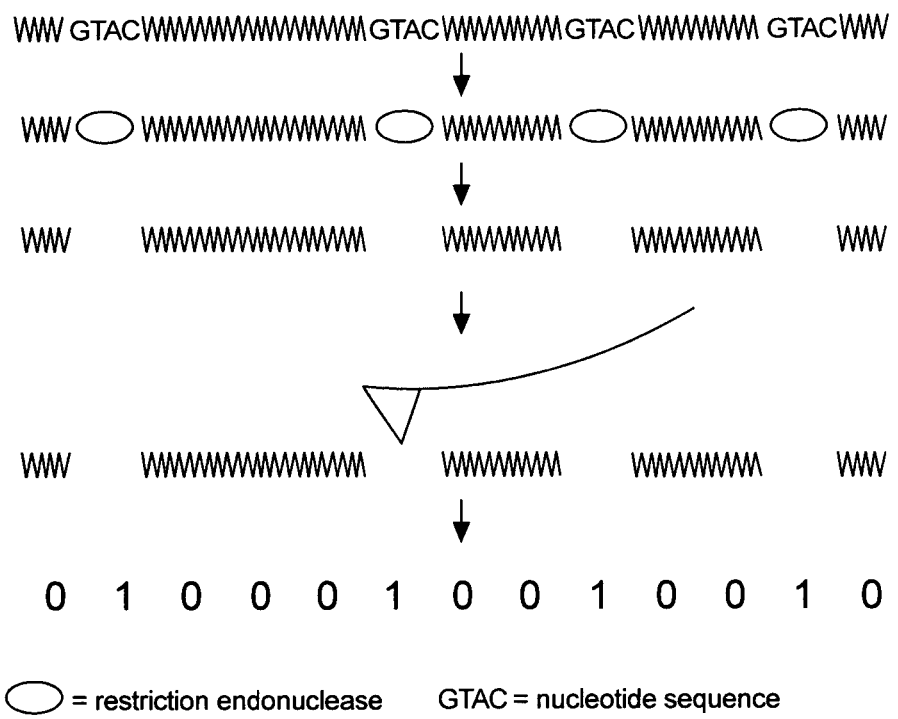
FIGS. 1A and 1B depict an experimental scheme for single molecule DNA profiling using restriction endonucleases.

As used herein, "nucleic acid" refers to either DNA or RNA, single-stranded or double-stranded, and any chemical modifications thereof. Modifications include, but are not limited to, those which provide other chemical groups that incorporate additional charge, polarizability, hydrogen bonding, electrostatic interaction, and functionality to the nucleic acid. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "body fluid" and "bodily fluid," used interchangeably herein, refer to a biological sample of liquid from a mammal, e.g., from a human. Such fluids include aqueous fluids such as serum, plasma, lymph fluid, synovial fluid, follicular fluid, seminal fluid, amniotic fluid, milk, whole blood, urine, cerebrospinal fluid, saliva, sputum, tears, perspiration, mucus, tissue culture medium, tissue extracts, and cellular extracts. Particular bodily fluids that are of interest in the context of the present invention include serum, plasma, and blood.

Nucleic acid hybridization reactions can be performed under conditions of different "stringency". Conditions that increase stringency of a hybridization reaction of widely known and published in the art. See, e.g., Sambrook et al. *Molecular Cloning, A Laboratory Manual,* 2nd Ed., Cold Spring Harbor Laboratory Press, Cold Spring Harbor, N.Y., 1989, herein incorporated by reference. For example, see page 7.52 of Sambrook et al. Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where 1×SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 1×SSC (150 mM NaCl, 15 mM sodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C. As another example, stringent hybridization conditions comprise: prehybridization for 8 hours to overnight at 65° C. in a solution comprising 6× single strength citrate (SSC) (1×SSC is 0.15 M NaCl, 0.015 M Na citrate; pH 7.0), 5× Denhardt's solution, 0.05% sodium pyrophosphate and 100 µg/ml herring sperm DNA; hybridization for 18-20 hours at 65° C. in a solution containing 6×SSC, 1× Denhardt's solution, 100 µg/ml yeast tRNA and 0.05% sodium pyrophosphate; and washing of filters at 65° C. for 1 hour in a solution containing 0.2×SSC and 0.1% SDS (sodium dodecyl sulfate).

Stringent hybridization conditions are hybridization conditions that are at least as stringent as the above representative conditions. Other stringent hybridization conditions are known in the art and may also be employed to identify nucleic acids of this particular embodiment of the invention.

A polynucleotide has a certain percent "sequence identity" to another polynucleotide, meaning that, when aligned, that percentage of bases are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments, with a restricted affine gap penalty model. See *Meth. Mol. Biol.* 70: 173-187 (1997). Also, the GAP program using the Needleman and Wunsch alignment method can be utilized to align sequences using a general class of gap models. See *J. Mol. Biol.* 48: 443-453 (1970).

A "computer-based system" refers to the hardware means, software means, and data storage means used to analyze information. The minimum hardware of a subject computer-based system comprises a central processing unit (CPU), input means, output means, data storage means, access to the Internet and data available therein. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" or "computing means" references any hardware and/or software combination that will perform the functions required of it. For example, any processor herein may be a programmable digital microprocessor such as available in the form of an electronic controller, mainframe, server, parallel computer, cluster computer, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

By "clinical assay" is meant an assay or test that is performed on a sample obtained from an individual or patient (also referred to herein as host or subject) in order to provide information on current or future health or condition, diagnosis, treatment, prevention, and/or monitoring of a condition of the individual or patient.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an insoluble support" includes a plurality of such supports and reference to "the immobilized nucleic acid" includes reference to one or more immobilized nucleic acids and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of detecting a nucleic acid analyte in a sample. The methods generally involve modifying immobilized nucleic acids from a sample onto an insoluble support in a substantially elongated configuration, where modification generates an identifying feature that identifies the analyte; and detecting the identifying feature(s) using scanning probe microscopy, to detect the analyte. The present invention further provides a method for assigning a profile of a feature to a nucleic acid. The present invention further provides a computer program product for use in a subject method. The present invention further provides a system for detecting a nucleic acid in a sample; and a system for assigning a profile of a feature to a nucleic acid. The present invention further provides a method for immobilizing a nucleic acid onto an insoluble support; and further provides insoluble support having nucleic acid(s) immobilized thereon. The present invention further provides a method of diagnosing a disorder or condition in an individual, where the method involves use of a subject method for detecting a nucleic acid analyte.

Method of Detecting a Nucleic Acid in a Sample

The present invention provides methods of detecting a nucleic acid analyte in a sample. The methods generally involve: a) modifying immobilized nucleic acids from the sample onto an insoluble support, such that the nucleic acids are immobilized in a substantially elongated configuration, where the modification generates one or more identifying features that identify the analyte; and b) detecting the one or more identifying features using scanning probe microscopy to detect the presence of the nucleic acid analyte in the sample.

Any type of scanning probe microscopy can be used to detect the identifying feature(s). In many embodiments, atomic force microscopy (AFM) is used. Using AFM, the lengths, in nanometers or micrometers, of the nucleic acids is determined. The lengths, in nanometers or micrometers, of the nucleic acids can then be converted to lengths in base pairs (bp). The conversion can be carried out manually, e.g., by a human. Alternatively, the conversion can be carried out by a computer program, as described below. In general, 0.33 bp is equivalent to about 1 nm; and 30 bp is equivalent to about 10 nm.

In some embodiments, the method is qualitative, e.g., detecting the presence of a nucleic acid in a sample indicates whether the nucleic acid is present. In other embodiments, the method is quantitative, e.g., the abundance of the nucleic acid in the sample is determined.

Nucleic Acid Modifications and Identifying Features

In many embodiments, the immobilized nucleic acid is modified in situ with one or more modifying agents, to generate identifying feature(s). Suitable modifying agents include, e.g., nucleotide sequence-specific modifying agents such as restriction endonucleases; methylation pattern-sensitive modifying agents, e.g., restriction endonucleases that digest DNA that is unmethylated, but that do not digest methylated DNA; enzymes that methylate DNA; a bisulfide (e.g., sodium bisulfite); a hybridizing nucleic acid; a nucleic acid-binding protein; detectable labels; and the like.

Restriction Endonucleases

In some embodiments, the modifying step involves contacting immobilized nucleic acids with one or more restriction endonucleases under conditions such that the immobilized nucleic acids are cleaved by the restriction endonucleases, and immobilized restriction fragments are generated. In these embodiments, the identifying feature is a restriction endonuclease pattern. The restriction endonuclease pattern is detected using SPM (e.g., AFM), where a gap generated by the restriction endonuclease is detected. The AFM tip rasters along the lengths of the immobilized restriction fragments and detects gaps (e.g., restriction endonuclease cleavage sites). The distance between two gaps is a restriction fragment length.

Suitable restriction endonucleases include restriction endonucleases that recognize four-nucleotide sequences; restriction endonucleases that recognize six-nucleotide sequences; restriction endonucleases that recognize eight-nucleotide sequences; and the like. A wide variety of restriction endonucleases are known in the art; any restriction endonuclease can be used. Examples of literature sources of restriction endonucleases and their recognition sequences include: Burrell M. M., ed. (1993). *Enzymes of Molecular Biology*. Humana Press Inc., New York; and Kessler C., et. al. (1985). Recognition sequences of restriction endonucleases and methylases—a review. *Gene* 33: 1-102.

In many embodiments, the immobilized nucleic acid is contacted in situ with one or more restriction endonucleases, under conditions that permit cleavage of the nucleic acid with the restriction endonuclease(s). The restriction endonucleases generate gaps in the immobilized nucleic acid, generating restriction fragments. The length of the restriction fragments is measured as the distance between the gaps. Typically, the length of the restriction fragments is measured using atomic force microscopy.

Using AFM, the contour lengths, in nanometers or micrometers, of the restriction fragments is determined. The lengths, in nanometers or micrometers, of the restriction fragments can then be converted to lengths in base pairs (bp). The conversion can be carried out manually, e.g., by a human. Alternatively, the conversion can be carried out by a computer program, as described below. In general, 0.33 bp is equivalent to about 1 nm; and 30 bp is equivalent to about 10 nm.

Methylation

In some embodiments, the modifying step involves contacting immobilized nucleic acids with one or more agents that methylate DNA, where the contacting provides for methylation of the DNA. In these embodiments, the identifying feature is a methylation pattern. Detection of the methylation pattern will in many embodiments involve cleaving the methylated DNA with one or more restriction endonucleases that discriminate between methylated and unmethylated DNA. The pattern of gaps generated by the action of the restriction endonucleases is detected as described above for restriction fragments.

Methylating agents include bisulfide agents, many of which are known in the art. Restriction endonucleases that discriminate between methylated and unmethylated DNA are known in the art; and any known endonuclease can be used. As one non-limiting example, MboI does not cleave the sequence G$^m$ATC (where $^m$A is methylated adenine), while Sau3AI does cleave G$^m$ATC. Similarly, HpaII does not cleave C$^m$CGG, while MspI does cleave C$^m$CGG. Other methylation pattern-sensitive restriction endonucleases are known in the art. See., e.g, McClelland et al. (1994) *Nucleic Acids Res.* 22(17):3640-59.

Hybridization with a Nucleic Acid Probe

In some embodiments, the modifying step involves contacting immobilized nucleic acids with one or more nucleic acid probes under conditions that favor or promote hybridization of the nucleic acid probe with the immobilized nucleic acids. In these embodiments, the identifying feature is hybridization, and detecting the identifying feature involves detecting a height difference between unhybridized immobilized nucleic acid and hybridized immobilized nucleic acid.

A hybridizing nucleic acid (a "nucleic acid probe") is a nucleic acid that hybridizes with an immobilized nucleic acid. Suitable nucleic acid probes include DNA; RNA; peptide nucleic acid (PNA); locked nucleic acid (LNA); and the like. PNA is described in numerous publications, including, e.g., Paulasova and Pellestor (2004) *Ann. Genet.* 47:349-358; and "Peptide Nucleic Acids: Protocols and Applications" (2004) $2^{nd}$ Edition, P. E. Nielsen, Ed., Horizon Bioscience. LNA is described in numerous publications, including, e.g., Vester and Wengel (2004) *Biochem.* 43:13233-41; and Petersen and Wengel (2003) *Trends Biotechnol.* 21:74-81.

In some embodiments, a modifying agent is a nucleic acid that hybridizes under stringent hybridization conditions to an immobilized nucleic acid. Nucleic acid probes can be of various lengths, e.g., from about 5 nucleotides to about 100 nucleotides in length, e.g., from about 5 nucleotides to about 10 nucleotides, from about 10 nucleotides to about 15 nucleotides, from about 15 nucleotides to about 20 nucleotides, from about 20 nucleotides to about 25 nucleotides, from about 25 nucleotides to about 30 nucleotides, from about 30 nucleotides to about 50 nucleotides, from about 50 nucleotides to bout 75 nucleotides, or from about 75 nucleotides to about 100 nucleotides in length. Nucleic acid probes can be generated using any known method, e.g., chemical synthesis; cleavage of a nucleic acid with one or more restriction endonucleases to generate fragments, where a fragment may be purified by, e.g., gel electrophoresis; recombinant methods; and the like.

Binding with a Nucleic Acid Binding Protein

In some embodiments, the modifying step involves contacting immobilized nucleic acids with one or more proteins that bind DNA, under conditions that favor DNA-protein binding. In these embodiments, the identifying feature is binding of the protein(s) to the immobilized nucleic acid, and detecting the identifying feature involves detecting a height difference between immobilized nucleic acid without bound protein and immobilized nucleic acid with bound protein. DNA-binding proteins include, but are not limited to, histones, transcription factors, DNA polymerases, RNA polymerases, and the like.

Modification with Detectable Label

In some embodiments, the modifying step involves modifying immobilized nucleic acids with one or more labeling agents. In these embodiments, the identifying feature is labeled immobilized nucleic acid, and detecting the identifying feature involves detecting a height difference between labeled immobilized nucleic acid and unlabeled immobilized nucleic acid.

Suitable labeling agents include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA); detectable proteins; biotin; antibodies; engineered nanoparticles of known dimensions; polymer chains of known dimensions; non-fluorescent nucleic acids of any length; and the like. Detectable labels also include peptides (e.g., epitope tags) or polypeptides that can be detected by antibody binding, e.g., by binding of a detectably labeled antibody or by detection of bound antibody.

Suitable fluorescent proteins and chromogenic proteins include, but are not limited to, a green fluorescent protein (GFP), including, but not limited to, a GFP derived from *Aequoria Victoria* or a derivative thereof, e.g., a "humanized" derivative such as Enhanced GFP, which is available commercially, e.g., from Clontech, Inc.; a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from *Anthozoan* species, as described in, e.g., Matz et al. (1999) *Nature Biotechnol.* 17:969-973; and the like.

Also suitable for use are quantum dots (e.g., detectably labeled semiconductor nanocrystals, such as fluorescently labeled quantum dots, antibody-conjugated quantum dots, and the like). See, e.g., Dubertret et al. 2002 *Science* 298:759-1762; Chan et al. (1998) *Science* 281:2016-2018; U.S. Pat. No. 6,855,551; Bruchez et al. (1998) Science 281:2013-2016.

Nucleic Acids

Nucleic acids that are suitable for detection and/or analysis using a subject method include, but are not limited to, genomic DNA; complementary DNA (cDNA; e.g., a reverse-transcribed copy of an mRNA); ribosomal RNA; short interfering RNA (siRNA); a ribozyme; transfer RNA (tRNA); spliced mRNA; a cDNA copy of a splice mRNA; unspliced mRNA; a cDNA copy of an unspliced mRNA; and the like. Suitable nucleic acids include naturally-occurring nucleic acids; synthetic nucleic acids; recombinant nucleic acids; and the like. Suitable nucleic acids further include nucleic acid libraries; nucleic acids generated by subtractive hybridization techniques; nucleic acids separated by an Electrophoretic method, e.g., gel electrophoresis; nucleic acids isolated using flow cytometry; and the like.

The nucleic acid in the sample that is immobilized onto the surface of an insoluble support can be of any length, e.g., from about 20 base pairs to about 50,000 base pairs, e.g., from about 20 base pairs to about 50 bp, from about 50 bp to about 100 bp, from about 100 bp to about 500 bp, from about 500 bp to about 1,000 bp, from about 1,000 bp to about 2,000 bp, from about 2,000 bp to about 5,000 bp, from about 5,000 bp to about 10,000 bp, from about 10,000 bp to about 25,000 bp, or from about 25,000 bp to about 50,000 bp, or longer than 50,000 bp. In many embodiments, the nucleic acid in the sample is in the length range of mRNA molecules, e.g., from about 500 bp to about 5,000 bp, e.g., from about 500 bp to about 5,000 bp, from about 500 bp to about 4,000 bp, from about 500 bp to about 3,000 bp, from about 500 bp to about 2,000 bp, or from about 1,000 bp to about 5,000 bp.

In some embodiments, as discussed above, the modifying step generates nucleic acid fragments, e.g, restriction fragments. Typically the immobilized nucleic acid fragments have lengths in a range of from about 5 bp to about 2,000 bp, e.g., from about 5 bp to about 25 bp, from about 25 bp to about 50 bp, from about 50 bp to about 75 bp, from about 75 bp to about 100 bp, from about 100 bp to about 150 bp, from about 150 bp to about 200 bp, from about 200 bp to about 300 bp, from about 300 bp to about 400 bp, from about 400 bp to about 500 bp, from about 500 bp to about 1,000 bp, from about 1,000 bp to about 1,500 bp, or from about 1,500 bp to about 2,000 bp. Using a subject method, fragments as small as about 5 bp in length can be detected and measured.

The contour length of the immobilized nucleic acid fragments is initially expressed in nanometers. Typically the immobilized nucleic acid fragments have lengths in a range of from about 5 nm to about 700 nm, e.g., from about 5 nm to about 10 nm, from about 10 nm to about 20 nm, from about 20 nm to about 50 nm, from about 50 nm to about 75 nm, from about 75 nm to about 100 nm, from about 100 nm to about 125 nm, from about 125 nm to about 150 nm, from about 150 nm to about 175 nm, from about 175 nm to about 200 nm, from about 200 nm to about 250 nm, from about 250 nm to about 500 nm, from about 500 nm to about 600 nm, or from about 600 nm to about 700 nm. The limit of resolution of the instant method is approximately 1 nm.

The sample containing nucleic acids will in many embodiments include more than one nucleic acid species. The nucleic acids that are immobilized onto the surface of an insoluble support can include from 2 to about $10^5$ distinct species, e.g., the nucleic acids will in many embodiments include from 2 to about 5, from about 5 to about 10, from about 10 to about 50, from about 50 to about $10^2$, from about $10^2$ to about $5 \times 10^2$, from about $5 \times 10^2$ to about $10^3$, from about $10^3$ to about $5 \times 10^3$, from about $5 \times 10^3$ to about $10^4$, from about $10^4$ to about $5 \times 10^4$, or from about $5 \times 10^4$ to about $10^5$ different nucleic acid species. The term "different nucleic acid species" refers to nucleic acids that differ from one another in nucleotide sequence by at least one nucleotide, e.g., two nucleic acids are different species if they differ from one another in nucleotide sequence by 1, 2, 3, 4, 5, 6-10, 11-15, 16-20, 21-25, or 26-30, or more, nucleotides.

A subject method detects a single nucleic acid analyte in a sample in which the nucleic acid analyte being detected is present at a frequency of from about 1 in 10 nucleic acid species to about 1 in 50 nucleic acid species, from about 1 in 50 nucleic acid species to about 1 in $10^2$ nucleic acid species, from about 1 in about $10^2$ nucleic acid species to about 1 in 500 nucleic acid species, from about 1 in 500 nucleic acid species to about 1 in $10^3$ nucleic acid species, from about 1 in $10^3$ nucleic acid species to about 1 in $5 \times 10^3$ nucleic acid species, from about 1 in $5 \times 10^3$ nucleic acid species to about 1 in $10^4$ nucleic acid species, from about 1 in $10^4$ nucleic acid species to about 1 in $10^5$ nucleic acid species, or from about 1 in $10^5$ nucleic acid species to about 1 in $10^6$ nucleic acid species.

Nucleic acids are immobilized onto the surface of an insoluble support in substantially elongated configuration; the immobilized nucleic acid strands are modified; and following modification, the immobilized nucleic acid strands are scanned using SPM. The density of the immobilized nucleic acid strands is from about 1 strand per $\mu m^2$ to about 100 strands per $\mu m^2$, e.g., from about 1 strand per $\mu m^2$ to about 5 strands per $\mu m^2$, from about 5 strands per $\mu m^2$ to about 10 strands per $\mu m^2$, from about 10 strands per $\mu m^2$ to about 25 strands per $\mu m^2$, from about 25 strands per $\mu m^2$ to about 50 strands per $\mu m^2$, from about 50 strands per $\mu m^2$ to about 75 strands per $\mu m^2$, or from about 75 strands per $\mu m^2$ to about 100 strands per $\mu m^2$.

Samples

The nucleic acids that are immobilized on an insoluble support are from any of a variety of samples, including biological samples. In some embodiments, the sample is a single cell. In many embodiments, the sample is a biological sample, e.g., a biopsy sample, a tissue sample, a bodily fluid sample, and the like. The sample will in many embodiments include cells, e.g., nucleated cells. In other embodiments, the sample will include nucleic acids in the absence of cells (e.g., a "cell-free" sample).

Insoluble Support

The insoluble support (also referred to as the "substrate") can in any of a variety of shapes and sizes. A suitable insoluble support may be planar; spherical; etc. The insoluble support may be in the form of a disk or a sheet, and may comprise a square surface, a circular surface, a rectangular surface, etc.

The insoluble support will in some embodiments comprise patterns such as a grid. The insoluble support will in some embodiments comprise one or more spatial address. The insoluble support will in some embodiments have features such as channels (e.g., microchannels, nanochannels), ridges, pores, and the like. The insoluble support can be transparent, translucent, or opaque.

The surface of the insoluble support onto which the nucleic acids are immobilized retains nucleic acids. In some embodiments, the surface comprises a nucleic acid protection layer adsorbed onto the surface, which layer protects the immobilized nucleic acids from degradation. In some embodiments, the nucleic acid protection layer includes one or more agents that inhibit nucleic acid degradation. For example, in some embodiments, the nucleic acid protection layer includes one or more nuclease inhibitors. RNase inhibitors include, e.g., diethylpyrocarbonate.

The surface of the insoluble support onto which the nucleic acids are immobilized allows for one or more modification steps and/or other steps (e.g., washing), while maintaining the capacity to retain small nucleic acids. The surface of the insoluble support onto which the nucleic acids are immobilized also allows for one or more drying steps. The surface of the insoluble support onto which the nucleic acids are immobilized does not exhibit any undesired chemical or electronic interaction with an AFM tip.

The surface of the insoluble support onto which the nucleic acids are immobilized is smooth. The surface has contour irregularities that are less than 2 mm, e.g., less than about 1.5 nm, or less than about 1 nm in height. The surface has a root mean square (RMS) roughness of less than about 2.0 nm, less than about 1.8 nm, less than about 1.5 nm, less than about 1.4 mm, e.g., less than about 1.2 nm, less than about 1.0 mm, less than about 0.8 nm, less than about 0.6 nm, or less than about 0.5 nm, e.g., about 0.4 nm.

The surface the insoluble support onto which the nucleic acids are immobilized is any surface that has an rms roughness less than about 2.0 nm. Suitable materials include, but are not limited to, mica; derivatized mica; polished silicon; and the like. Suitable mica includes muscovite mica (also known as granitic mica) and phlogopite mica.

Nucleic acids are immobilized or deposited onto the surface of an insoluble support in a substantially elongated configuration. Any method for immobilizing or depositing a nucleic acid onto the surface of an insoluble support in a substantially elongated configuration can be used, including, e.g., application of an electric field; application of a magnetic field; application of a fluid shear field; thermal expansion; chemical methods that promote elongated configuration; application of a mechanical force (e.g., centrifugal force; use of optical or magnetic tweezers; use of a deformable substrate); and the like. Exemplary methods include, but are not limited to, fluid fixation (Jing et al. (1998) *Proc. Natl. Acad. Sci. USA* 95:8046-8051); fixation by application of an electrical field; fixation by traveling meniscus (Michalet et al. (1997) *Science* 277:1518-1523); end tethering of nucleic acids with beads (Strick et al. (1996) *Science* 271:1835-1837); and the like. Various publications exist that describe techniques for elongating nucleic acids. See, e.g., U.S. Pat. No. 6,610,256.

The surface of the insoluble support onto which nucleic acids are immobilized retains nucleic acids (e.g., modified nucleic acids such as restriction fragments) as short as 10 nucleotides or base pairs, 15 nucleotides or base pairs, 20 nucleotides or base pairs, 25 nucleotides or base pairs, 30 nucleotides or base pairs, 40 nucleotides or base pairs, or as short as 50 nucleotides or base pairs in length.

Nucleic acids are immobilized onto the surface of an insoluble support by chemical and/or physical means. The surface of the insoluble support will in some embodiments be chemically modified such that: 1) nucleic acids are immobilized onto the surface; 2) binding of the nucleic acids on the surface does not interfere with modification of the immobilized nucleic acids; and 3) modified nucleic acids are retained on the surface. In other embodiments, the surface of the insoluble support is physically modified such that 1) nucleic acids are immobilized onto the surface; 2) binding of the nucleic acids on the surface does not interfere with modification of the immobilized nucleic acids; and 3) modified nucleic acids are retained on the surface. In other embodiments, nucleic acids are immobilized onto the surface of an insoluble support by "nano-anchors," e.g., by a securing agent, as described in more detail below.

Chemical Modification of the Nucleic Acid-Binding Surface of the Insoluble Support In some embodiments, the surface of the insoluble support onto which nucleic acids are immobilized is chemically modified to retain nucleic acids as short as 10 (or 15, 20, 25, 30, 40, or 50) nucleotides or base pairs in length. Chemical modification of the surface of the insoluble support is generally carried out by reacting the surface of the insoluble support with a linking agent. A suitable linking agent comprises a moiety that binds to the surface of the insoluble support (an insoluble support surface binding moiety); and a moiety that binds to the nucleic acid (a nucleic acid binding moiety). "Binding" includes covalent binding and non-covalent binding, where non-covalent binding includes linkage via electrostatic interaction, ionic interaction, van der Waals forces, hydrogen bonding, and the like.

In some embodiments, a linking agent is a silane compound, e.g., an organosilane such as a glycidoxypropyltrimethoxysilane or an aminopropyltriethoxysilane. In some embodiments, a linking agent comprises a silane moiety that binds to a mica surface; and an organic moiety that binds to a nucleic acid (e.g., covalently or non-covalently binds nucleic acid). An organic moiety that binds to a nucleic acid will in some embodiments comprise an amino group or a primary amine. Suitable silane compounds include, but are not limited to, epoxy-silane, 3-aminopropyl triethoxysilane (APTES), 3-glycidoxypropyltrimethoxy silane, vinyl silane, chlorosilane, and the like.

In some embodiments, nucleic acids are immobilized onto the surface by charge, e.g., the surface of the insoluble support is derivatized such that it has a net positive charge. In some embodiments, the surface is derivatized using APTES.

Physical Modification of the Nucleic Acid-Binding Surface of the Insoluble Support In some embodiments, the surface of the insoluble support onto which nucleic acids are immobilized is physically modified, such that the nucleic acid is held on the surface by weak bonds. The surface can be modified to include channels or grooves into which a nucleic acid is deposited.

Method for Immobilizing a Nucleic Acid; Insoluble Supports

The present invention further provides methods for immobilizing a nucleic acid or other polymer (e.g., a biopolymer, a non-biological polymer) onto an insoluble support. The method generally involves: a) depositing a nucleic acid onto a surface of an insoluble support, where the nucleic acid is deposited in a substantially elongated configuration; b) applying a shadow mask onto the deposited nucleic acid, where the shadow mask comprises at least one linear gap; and c) depositing a securing material onto the deposited nucleic acid through the gap, thereby immobilizing the deposited nucleic acid.

In some embodiments, shadow mask comprises a single linear gap. In other embodiments, the shadow mask comprises a plurality of linear gaps. Typically the gaps are from about 5 nm to about 20 nm wide. In many embodiments, the shadow mask comprises a plurality of parallel linear gaps. In many embodiments, the shadow mask is applied such that the linear gap(s) is substantially perpendicular to the nucleic acid.

Where the shadow mask comprises a plurality of gaps, the gaps are generally from about 75 nm to about 250 nm apart, e.g., from about 75 nm to about 100 nm, from about 100 nm to about 125 mm, from about 125 nm to about 150 nm, from about 150 nm to about 175 nm, from about 175 nm to about 200 nm, from about 200 nm to about 225 nm, or from about 225 nm to about 250 nm apart.

The securing material is generally an inert metal. Suitable securing materials include, but are not limited to, gold, platinum, titanium, rhodium, nickel-cobalt alloys, and the like. In some embodiments, the securing material is gold. In other embodiments, the securing material is platinum. The securing material is typically substantially elongate (e.g., a wire).

The insoluble support is generally as described above. In some embodiments, the insoluble support is derivatized to generate a positively charged surface. In many embodiments, the insoluble support comprises mica. In many embodiments, the insoluble support has an rms roughness of less than about 1.4 nm, e.g., less than about 1.2 nm, less than about 1.0 nm, less than about 0.8 nm, less than about 0.6 nm, or less than about 0.5 nm, e.g., about 0.4 nm.

The present invention further provides an insoluble support generated using a subject method. A subject insoluble support comprises a nucleic acid immobilized onto the surface of the insoluble support by a securing agent.

Nucleic Acid Profiling

The present invention provides a method for assigning a profile of a feature to a nucleic acid. The method generally involves modifying an immobilized nucleic acid with one or more nucleic acid modifying agents, where the nucleic acid is immobilized onto an insoluble support in a substantially elongated configuration, where the modification generate a modification feature; detecting the modification feature of the immobilized nucleic acid using atomic force microscopy; and assigning a character to each modification feature, thereby generating a profile of the feature (a "feature profile"). A feature profile refers to the location, order, or pattern of a feature.

In many embodiments, the feature profile generated is compared with a reference. In other embodiments, two or more profiles are compared with one another. In other embodiments, clusters of profiles are compared.

Profiles of modification features include, but are not limited to, restriction endonuclease digestion pattern; methylation pattern; nucleic acid hybridization pattern; protein binding pattern; a binding pattern of any binding element (e.g., a nucleic acid probe; a nanoparticle; a protein; a dye); and the like.

In many embodiments, a profile comprises two or more different features. In some embodiments, a first feature is assigned a zero; and a second feature is assigned a non-zero bit. As one non-limiting example, an immobilized nucleic acid is digested with a restriction endonuclease, generating immobilized nucleic acid fragments. A first modification feature is a gap between two adjacent nucleic acid fragments, and is represented by a non-zero bit, e.g., a 1. A second modification feature is the contour length, in nanometers, of a nucleic acid fragment (e.g., the distance between two gaps), and is represented by one or more zeros, where the number of zeros is proportional to the length of the nucleic acid fragment. In this manner, a bar code is generated.

Computer Program Products

The present invention further provides a computer program product for carrying out a subject method. In some embodiments, the present invention provides a computer program product for measuring the length of an immobilized nucleic acid and/or carrying out the conversion from length of a nucleic acid as determined by AFM to length of a nucleic acid, in base pairs; such a computer program product is useful in methods and systems for detecting a nucleic acid. In other embodiments, the present invention provides a computer program product for assigning a profile of a feature to a nucleic acid; such a computer program product is useful in methods and systems for assigning a profile of a feature to a nucleic acid.

Detecting a Nucleic Acid

In some embodiments, the present invention provides a computer program product for measuring the length of an immobilized nucleic acid and/or carrying out the conversion from length of a nucleic acid as determined by AFM to length of a nucleic acid, in base pairs. The present invention thus provides a computer program product including a computer readable storage medium having a computer program stored on it. The program, when read by a computer, measures the length of an immobilized nucleic acid and/or executes conversion from length (e.g., length in nanometers) of a nucleic acid as determined by AFM to length of a nucleic acid, in base pairs. The computer program product has stored therein a computer program for performing the conversion. In some embodiments, the computer program product will compare the length of an immobilized nucleic acid to a reference. In other embodiments, the computer program product will calculate the abundance of the nucleic acid in the sample. In other embodiments, the computer program product will calculate the proportion of the nucleic acid in the sample, compared to the total number of nucleic acid species in the sample.

In some embodiments, a subject computer program product will carry out one or more of the following: 1) computation of the nucleic acid length in base pairs; 2) comparison of the calculated nucleic acid length, in base pairs, to a reference; 3) detection of the number of nucleic acids in a sample; 4) calculation of the proportion of a given nucleic acid analyte in a sample, compared to the total number of nucleic acids in the sample, or to the number of different nucleic acid species in the sample; 5) calculation of the total number of molecules of a given nucleic acid analyte in a sample; 6) comparison of the total number of molecules of a given nucleic acid analyte in a first sample with the total number of molecules of the nucleic acid in at least a second sample.

Assigning a Profile of a Feature

In some embodiments, the present invention provides a computer program product for assigning a profile of a feature. The computer program product includes a computer readable storage medium having a computer program stored on it. The program can, when read by a computer, carry out one or more of the following operations: 1) detect a feature of an immobilized nucleic acid; 2) assign a character, or a series of characters, to each feature; and 3) generate a profile of a feature. In some embodiments, the program can further compare two profiles with one another. In some embodiments, the program can further compare three or more profiles, and generate clusters of profiles.

In many embodiments, a subject computer program product generates a binary digital profile. As one non-limiting example, as discussed above, in some embodiments, the feature profile is a restriction endonuclease digestion pattern. A subject computer program product can carry out one or more of the following: 1) measure a length of an immobilized nucleic acid restriction fragment; 2) assign a character (e.g., a non-zero bit) to a gap between restriction fragments; 3) assign a character to a nucleic acid restriction fragment, based on the length of the fragment (e.g., assign one or more zeros to a fragment, where the number of zeros correlates with the length of the fragment); and 4) generate a restriction endonuclease digestion profile of the nucleic acid. In some embodiments, the computer program product will compare two restriction endonuclease digestion profiles. For example, in some embodiments, the computer program product will compare a test restriction endonuclease digestion profile with a reference restriction endonuclease digestion profile. As one non-limiting example, a reference restriction endonuclease digestion profile can be generated using a known nucleotide sequence of a known nucleic acid. As another non-limiting example, in some embodiments, the computer program will identify polymorphisms in a gene by comparing two (or more) restriction endonuclease digestion profiles. In other embodiments, the computer program product will compare three or more restriction endonuclease digestion profiles.

Reference Databases

In many embodiments, the computer program product will have stored thereon a reference database, or will access a stored reference database, where the reference database will include information about known features of known nucleic acids (e.g., nucleic acids of known nucleotide sequence). The reference database will in some embodiments include restriction patterns, for a plurality of restriction endonucleases, of a plurality of nucleic acids of known nucleotide sequence. In some embodiments, the reference database will include the nucleotide sequences of nucleic acids, such that the hybridization pattern of any given nucleic acid probe with known nucleic acids in the database can be used to compare the hybridization pattern of the nucleic acid probe with test nucleic acids immobilized on the insoluble support.

AFM Data Acquisition and Analysis

As noted above, in many embodiments, the SPM that is used to detect and/or analyze an immobilized nucleic acid is AFM. In some embodiments, the instant invention provides a computer program product comprising a fast acquisition data analysis algorithm for detecting features in modified, immobilized nucleic acids.

Typical AFM and SPM imaging involves rastering a tip across a surface line by line to record a series of shape profiles that are then combined to form a three dimensional representation of the surface topography. The raster pattern resembles the way a cathode ray tube television scans a beam. The process takes considerable time and this is dictated by the scan speed, the scan length and the number of lines recorded in the image.

The present invention provides a computer program product comprising a fast acquisition data analysis algorithm that provides for increased scan speed. The amount of time to scan an image, where the image is an insoluble support having immobilized thereon nucleic acids that have been modified, is reduced by at least about 5%, at least about 10%, at least about 15%, at least about 20%, at least about 25%, at least about 30%, at least about 40%, at least about 50%, or more. Thus, e.g., the amount of time required to scan an image is less than about 10 minutes/$\mu m^2$, less than about 9 minutes/$\mu m^2$, less than about 8 minutes/$\mu m^2$, less than about 7 minutes/$\mu m^2$; less than about 6 minutes/$\mu m^2$, less than about 5 minutes/$\mu m^2$, less than about 4 minutes/$\mu m^2$, or less than about 3 minutes/$\mu m^2$.

For example, the amount of time required to scan an image is from about 1 minutes/$\mu m^2$ to about 7 minutes/$\mu m^2$, e.g., from about 1 minute/$\mu m^2$ to about 2 minutes/$\mu m^2$, from about 2 minutes/$\mu m^2$ to about 3 minutes/$\mu m^2$, from about 3 minutes/$\mu m^2$ to about 4 minutes/$\mu m^2$, from about 4 minutes/$\mu m^2$ to about 5 minutes/$\mu m^2$, from about 5 minutes/$\mu m^2$ to about 6 minutes/$\mu m^2$, or from about 6 minutes/$\mu m^2$ to about 7 minutes/$\mu m^2$.

Most of the data in the scanned image are never actually used. This is because much of the surface of the insoluble support does not include an immobilized modified nucleic acid; instead, much of the surface of the insoluble support is bare regions of substrate. For example, if the surface of the insoluble support that includes immobilized modified nucleic acid is only 5% of the surface area, then 95% of the time taken to scan the image is effectively wasted time. In some embodiments, a subject computer program product comprises a fast acquisition data analysis algorithm that provides for accelerated scan speed in a region of the insoluble support having no nucleic acid immobilized thereof; and reduced speed in a region of the insoluble support having nucleic acid immobilized thereon. Thus, e.g., the algorithm provides for scanning an image at a first scan speed (speed of movement of the AFM tip) over a first region of the insoluble support, where the first region of the insoluble support has no nucleic acid immobilized thereon; and scanning at a second scan speed over a second region of the insoluble support, where the second region of the insoluble support has a nucleic acid immobilized thereon. The first scan speed is at least about 5%, at least about 10%, at least about 15%, at least about 20%, at least about 25%, at least about 30%, at least about 40%, at least about 50%, at least about 75%, at least about 100% (or 2-fold), at least about 2.5-fold, at least about 3-fold, at least about 4-fold, at least about 5-fold, at least about 10-fold, or greater, than the second scan speed. The second scan speed would in many embodiments be activated where the AFM tip detects a height difference above the rms roughness of the surface of the insoluble support. Thus, in many embodiments, a subject computer program product provides for modification or adjustment of the speed of the AFM tip, based on information acquired by the AFM tip on the height above rms roughness of the surface of the insoluble support.

The software controlling the STM system uses the data obtained above to position the tip above the immobilized nucleic acid strands and starts to follow the approximate path of each strand. The cross-sectional profile of an immobilized nucleic acid is a "hill" with Gaussian or normal distribution. For optimal performance, the AFM tip should remain on the "top" or peak or maximum of the Gaussian distribution, so that the tip remains on the immobilized nucleic acid. To ensure that the tip (e.g., AFM tip) faithfully records the height profile along the actual top of the immobilized nucleic acid and does not wander off to the side, 2, 3, or 4 data points in the X lateral direction are recorded and then statistically fitted to the underlying cross-sectional model profile to predict the peak. Ideally these points should correspond to the two sides of the immobilized nucleic acid close to the substrate and the central point on the maximum height position. The actual values of these data points provide information on the alignment of the center point with respect to the immobilized nucleic acid chain's maximum height. These data, combined with similar data on previous scans, are then used to predict the position of the next three points as the AFM moves accurately along the top of the DNA chain. In this way an accurate profile of the DNA is obtained. For example, in a DNA molecule, one micron long 512 points would enable the entire chain to be mapped in 2 nm steps. The actual number of data points in this example would be 3×512 for typical parameter values.

In some embodiments, a subject computer program product comprises an algorithm that provides for acquiring 2, 3, or 4 cross-sectional profile data points at a given lateral position along a strand of immobilized nucleic acid. In some embodiments, a subject computer program product comprises an algorithm that provides for acquiring 2, 3, or 4 lateral data points at a first position, and at least a second position along a strand of immobilized nucleic acid. The distance between the first and at least the second position is from about 2 nm to about 100 nm, e.g., from about 2 nm to about 3 nm, from about 3 nm to about 5 nm, from about 5 nm to about 7 nm, from about 7 nm to about 10 nm, from about 10 nm to about 25 nm, from about 25 nm to about 50 nm, or from about 50 nm to about 100 nm. In some embodiments, a subject computer program product comprises an algorithm that provides for correction or adjustment of the tip position, based on the cross-sectional profile data points. For example, where one or more cross-sectional profile data points indicate that the tip is off the "peak" of the parabolic cross-sectional profile of the immobilized nucleic acid, the computer program product provides for adjustment of the tip position such that it is re-centered on the peak.

Computational Analysis

The present invention provides a computer program stored on a computer-readable storage medium, which program, when read by a computer, executes one or more of the following: 1) feature recognition from AFM metrological data (e.g., position of a feature, pattern of a feature, and the like); 2) generation of a profile of a feature (e.g., a restriction map; a methylation pattern; a binding pattern of a DNA-binding protein; etc.); 3) comparing a feature profile with a profile in a reference database; 4) storage of data, e.g., feature data, feature profile, etc.; 5) provides feedback to an AFM, e.g., to adjust scan speed, to select immobilized nucleic acids for scanning, etc.

Feature recognition includes, but is not limited to, recognizing a restriction site; recognizing a restriction endonuclease pattern; recognizing a start point of an individual nucleic acid strand (e.g., a nucleic acid molecule, a modified nucleic acid molecule, a restriction fragment, etc.); recognizing the end point of an individual nucleic acid strand (e.g., a nucleic acid molecule, a modified nucleic acid molecule, a restriction fragment, etc.); recognizing a methylation site; recognizing a methylation pattern; recognizing an element or moiety bound to a nucleic acid; recognizing a binding pattern of an element or moiety bound to a nucleic acid; and the like. Recognition of local features will in some embodiments be at the pixel scale by local rules, e.g., filter functions, kernel functions, and the like. Recognition of global features will in some embodiments by at image scale, e.g., by combining local features using local rules. Recognition of global features will in some embodiments by at image scale, e.g., by combining local features to optimize a score function. The score function will in some embodiments be a likelihood function that two adjacent local features belong to the same global feature as a neighbor. In some embodiments, a subject computer program will compute various statistics and confidence parameters for a recognized feature.

In some embodiments, a subject computer program will create a feature profile of each individual nucleic acid molecule. Thus, e.g., a subject computer program will in some embodiments create a restriction map; a methylation pattern; a binding pattern of an element (e.g., a protein, a nanoparticle, a dye, a nucleic acid probe) bound to a nucleic acid; and the like. In some embodiments, a subject computer program will store a feature profile, e.g., will store a plurality of feature profiles.

In some embodiments, a subject computer program will analyze a feature profile by comparing two or more feature profiles with one another. For example, in some embodiments, a subject computer program will compare a first feature profile with at least a second feature profile; and will computer their similarity. The similarity between a first feature profile and at least a second feature profile will in some embodiments be computed by aligning the first feature profile and the at least second feature profile with one another; and recording a score value of the best alignment. The score function will in some embodiments be the likelihood that the first profile and the at least second profile(s) are derived from the same molecule. The likelihood may be derived from a Bayesian prior modeling various noise processes, where noise processes include, e.g., sizing error, false negative, false positive, etc. The alignment is optimized using a dynamic programming algorithm. The similarity between a first feature profile and at least a second feature profile will in other embodiments be computed by comparing the output of a heuristic function applied to the feature profile. The applied heuristic function may be a discretization function; and its output a binary vector. The similarity may be measured by a distance function applied to the output binary vector. The distance function may be Hamming distance.

In some embodiments, a subject computer program will analyze a feature profile by grouping a plurality of feature profiles into clusters; and comparing a first cluster of feature profiles with at least a second cluster of feature profiles. In some embodiments, a subject computer program will analyze a plurality of feature profiles, e.g., feature profiles for a plurality of nucleic acid molecules; and determine a value for the fraction of an individual nucleic acid molecule (e.g., a nucleic acid analyte or a nucleic acid species) present in a given group of nucleic acids. In some embodiments, the computer program product will compute statistics and confidence parameters for the determined value. In some embodiments, a subject computer program will estimate the probability that a given nucleic acid species is present.

In some embodiments, a subject computer program will compare a feature profile to a database comprising nucleotide sequence data, restriction map data, and the like, for a plurality of nucleic acids of known nucleotide sequence. In some embodiments, comparison of a feature profile of a test nucleic acid to a reference database will provide the identity of the test nucleic acid.

In some embodiments, a subject computer program will store one or more of the following information: 1) the physical location of an immobilized nucleic acid on an insoluble support; 2) feature profile of an immobilized nucleic acid; and 3) identity of an immobilized nucleic acid. An insoluble support will in some embodiments include two or more addressable positions, which positions are recorded, along with information about a nucleic acid immobilized at the addressable position(s).

In some embodiments, a subject computer program will send information to an AFM to increase scan speed; to exclude one or more nucleic acids; and the like. For example, in some embodiments, a subject computer program will cause the AFM to ignore one or more nucleic acids, based on one or more selection criteria. Selection criteria may be based on recognition of one or more local and/or global features. In other embodiments, a subject computer program will cause the AFM to repeat a scan of a given nucleic acid.

Systems for Nucleic Acid Detection and Profiling

The present invention further provides a system for detecting a nucleic acid in a sample. The present invention further provides a system for assigning a profile of a feature to a nucleic acid.

Detecting a Nucleic Acid

In some embodiments, the present invention provides a system for detecting a nucleic acid in a sample. The system generally comprises: a) an atomic force microscope; b) a central computing environment; c) an input device operatively connected to the computing environment, to receive nucleic acid length data from the AFM; d) an algorithm (or computer program product) executed by the central computing environment (e.g., a processor), wherein the algorithm is executed based on the nucleic acid length data received by the input device, such that the computer program product executes one or more of: 1) computation of the nucleic acid length in base pairs; 2) comparison of the calculated nucleic acid length, in base pairs, to a reference; 3) detection of the number of nucleic acids in a sample; 4) calculation of the proportion of a given nucleic acid analyte in a sample, compared to the total number of nucleic acids in the sample, or to the number of different nucleic acid species in the sample; 5) calculation of the total number of molecules of a given nucleic acid analyte in a sample; 6) comparison of the total number of molecules of a given nucleic acid analyte in a first sample with the total number of molecules of the nucleic acid in at least a second sample.

The data input device (also referred to as an operator input device) may be, e.g., a keyboard, a mouse, and the like. The processor has access to a memory, which may be any suitable device in which the processor can store and retrieve data, such as magnetic, optical, or solid state storage devices (including magnetic or optical disks or tape or RAM, or any other suitable device). The processor can include a general purpose digital microprocessor (such as is typically used in a programmable computer) suitably programmed to execute an algorithm as described above, or any hardware or software combination which will perform the required functions.

In some embodiments, the data input device is coupled to a detection system such as an atomic force microscope (AFM), and the data are sent directly from the AFM to the data input device. In some embodiments, a subject system further includes a device for storing the input data. In some embodiments, a subject system further includes a library of references stored in a suitable storage medium. For example, the library of references will in some embodiments include restriction endonuclease digestion patterns of a wide variety of known nucleic acids.

The computer program can be recorded on computer readable media, e.g., any medium that can be read and accessed directly or indirectly by a computer. Such media include, but are not limited to: magnetic tape; optical storage such as compact disc-read only memory (CD-ROM) and digital versatile disk (DVD); electrical storage media such as random access memory (RAM) and read-only memory (ROM); and hybrids of these categories such as magnetic/optical storage media. One of skill in the art can readily appreciate how any of the presently known computer readable media can be used to create a manufacture that includes a recording of the present programming/algorithms for carrying out the above-described method. In certain embodiments, the programming is further characterized in that it provides a user interface, where the user interface presents to a user the option of selecting among one or more different, including multiple different, criteria. The instructions may include installation or setup directions. The instructions may include directions for use of the invention.

In addition, a subject system will typically include instructions for using the system to carry out a subject method. The instructions of the above-described system are generally recorded on a suitable recording medium. For example, the instructions may be printed on a substrate, such as paper or plastic, etc. As such, the instructions may be present in the system as a package insert, or components thereof (i.e. associated with the packaging or sub packaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the system, but means for obtaining the instructions from a remote source, e.g. via the Internet, are provided. An example of this embodiment is a system that includes a web address where the instructions can be viewed and/or from which the instructions can be downloaded. Conversely, means may be provided for obtaining the subject programming from a remote source, such as by providing a web address. Still further, the system may be one in which both the instructions and software are obtained or downloaded from a remote source, as in the Internet or World Wide Web. Some form of access security or identification protocol may be used to limit access only to those entitled to use the subject invention. As with the instructions, the means for obtaining the instructions and/or programming is generally recorded on a suitable recording medium.

Assigning a Profile of a Feature

In some embodiments, the present invention provides a system for assigning a profile of a feature to a nucleic acid.

The system generally comprises: a) an atomic force microscope, where the AFM detects a feature of a nucleic acid, e.g., a feature generated by modification of the nucleic acid; b) a central computing environment; c) an input device operatively connected to the computing environment, to receive nucleic acid length data from the AFM; d) an algorithm (or computer program product) executed by the central computing environment (e.g., a processor), wherein the algorithm is executed based on the nucleic acid length data received by the input device, such that the computer program product executes one or more of: 1) detecting a feature of an immobilized nucleic acid; 2) assigning a character, or a series of characters, to each feature; 3) generating a profile of a feature; 4) comparing two profiles with one another; and 5) comparing three or more profiles, and generating clusters of profiles.

The data input device (also referred to as an operator input device) may be, e.g., a keyboard, a mouse, and the like. The processor has access to a memory, which may be any suitable device in which the processor can store and retrieve data, such as magnetic, optical, or solid state storage devices (including magnetic or optical disks or tape or RAM, or any other suitable device). The processor can include a general purpose digital microprocessor (such as is typically used in a programmable computer) suitably programmed to execute an algorithm as described above, or any hardware or software combination which will perform the required functions.

In some embodiments, the data input device is coupled to a detection system such as an atomic force microscope (AFM), and the data are sent directly from the AFM to the data input device. In some embodiments, a subject system further includes a device for storing the input data. In some embodiments, a subject system further includes a library of references stored in a suitable storage medium. For example, the library of references will in some embodiments include restriction endonuclease digestion patterns of a wide variety of known nucleic acids.

The computer program can be recorded on computer readable media, e.g., any medium that can be read and accessed directly or indirectly by a computer. Such media include, but are not limited to: magnetic tape; optical storage such as CD-ROM and DVD; electrical storage media such as RAM and ROM; and hybrids of these categories such as magnetic/optical storage media. One of skill in the art can readily appreciate how any of the presently known computer readable media can be used to create a manufacture that includes a recording of the present programming/algorithms for carrying out the above-described method. In certain embodiments, the programming is further characterized in that it provides a user interface, where the user interface presents to a user the option of selecting among one or more different, including multiple different, criteria. The instructions may include installation or setup directions. The instructions may include directions for use of the invention.

In addition, a subject system will typically include instructions for using the system to carry out a subject method. The instructions of the above-described system are generally recorded on a suitable recording medium. For example, the instructions may be printed on a substrate, such as paper or plastic, etc. As such, the instructions may be present in the system as a package insert, or components thereof (i.e. associated with the packaging or sub packaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the system, but means for obtaining the instructions from a remote source, e.g. via the Internet, are provided. An example of this embodiment is a system that includes a web address where the instructions can be viewed and/or from which the instructions can be downloaded. Conversely, means may be provided for obtaining the subject programming from a remote source, such as by providing a web address. Still further, the system may be one in which both the instructions and software are obtained or downloaded from a remote source, as in the Internet or World Wide Web. Some form of access security or identification protocol may be used to limit access to those entitled to use the subject invention. As with the instructions, the means for obtaining the instructions and/or programming is generally recorded on a suitable recording medium.

Utility

The subject methods find use in a wide variety of research and diagnostic applications.

In some embodiments, a subject method for detecting the presence and/or amount of a nucleic acid analyte in a sample is useful for diagnosing a condition or disorder in an individual. In these embodiments, the nucleic acid analyte is one whose presence or amount is indicative of a condition or disorder. As one non-limiting example, the level of a given nucleic acid analyte will in some embodiments indicate that the cell is cancerous. In these embodiments, the present invention provides for detecting a cancerous cell in a sample.

In some embodiments, an insoluble support comprises a grid pattern onto which nucleic acids from various samples are immobilized. Each section of the grid will in many embodiments comprise a unique address (e.g., are positionally addressable). Additional information regarding each position on the grid may further be provided, e.g., information regarding one or more of: patient information; sample origin or type (e.g., tissue type, cell type, etc.); nature of the modifying agent (e.g., sequence identity of a nucleic acid probe; identity of the one or more restriction endonucleases; etc.); and the like. In some embodiments, two or more sections of the grid will include nucleic acids from the same sample; and each of the two or more sections will be modified with a different modifying agent. For example, in some of these embodiments, the two or more different modifying agents will comprise two or more different nucleic acid probes that identify different nucleic acid analytes. For example, the two or more different nucleic acid probes will identify different nucleic acids whose expression levels are increased in a particular type of cancer.

In some embodiments, a subject method of detecting a nucleic acid analyte comprises: a) modifying nucleic acids that are immobilized on an insoluble support with a first modifying agent, to generate a first identifying feature; b) detecting the first identifying feature using SPM; c) modifying the immobilized nucleic acids with a second modifying agent, to generate a second identifying feature; and d) and detecting the second identifying feature using SPM. This procedure can be repeated with third, fourth, etc. modifying agents, to generate third, fourth, etc., identifying features, which are then detected using SPM.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Celsius, and pressure is at or near atmospheric. Standard abbreviations may be used, e.g., bp, base pair(s); kb, kilobase(s); nt, nucleotide(s); aa, amino acid(s); pl, picoliter(s); s or sec, second(s); min, minute(s); h or hr, hour(s); i.m., intramuscular(ly); i.p., intraperitoneal(ly); s.c., subcutaneous(ly); and the like.

Example 1

Detecting Immobilized Nucleic Acid Fragments Using AFM

Materials and Methods

AFM. All AFM images were acquired with a Digital Instruments Bioscope AFM in tapping mode, using manufacturer-supplied TESP diving board cantilevers. Imaging was conducted at 22° C. and ~30% relative humidity. DNA was processed and imaged on freshly cleaved mica derivatized with 3-aminopropyl triethoxysilane to provide a positive charge for DNA retention, as previously described (18). SPIP (Scanning Probe Image Processor) image processing software (Image Metrology) was used to remove high frequency scan line noise in all AFM images and to manually measure DNA backbone length profiles.

DNA. A truncated splice variant of CD44, designated CD44v, along with the pOTB7 plasmid containing full length CD44 were obtained from ATCC. The CD44 plus pOTB7 sample was produced by double digestion with XhoI and EcoRI to release the cDNA insert from the pOTB7 vector. The CD44v cDNA sequence corresponds to Genbank accession number BC052287.1.

DNA digestion and mapping. Plasmid pEYFP-C1 (Clontech) was cut with NheI or StuI restriction endonucleases and diluted in 1× TE, pH 7.4, to 0.05 ng/µl. Linear DNA molecules were elongated and deposited onto derivatized surfaces using capillary fluid flow as described previously (18). Surface bound molecules were partially digested with PstI for 30 m at room temperature. Digested samples were washed with ultra pure water and dried under a stream of nitrogen gas. AFM images (2 µm×2 µm each; 20-70 images per sample) were taken from dried samples directly. Mapping of CD44v and OTB7 was done similarly. DNA sizing studies employed six linear fragments from pEYFP-C1, prepared by digestion in solution, deposited as described above, skipping the surface digestion and washing steps. The fragment sizes (nm/bp) were 191/579, 230/760, 447/1355, 589/1785, 788/2388, and 1561/4731. 0.33 nm/bp derived from the calculated pitch of B-DNA (17) was used as a nm-to-bp conversion factor.

Digestion efficiency. Both pOTB7 and CD44v were relatively short (594 nm/1800 bp) and loss or displacement of cleaved fragments during sample processing reduced the yield of measurable molecules. Molecules were deemed measurable if the ends were distinct, they contained one clear break, the fragments summed to full length, and the molecule was sufficiently elongated to manually follow the backbone contour. The digestion rate (% cleavage/total sites) varied from image to image but appeared to be above 50% on average.

Results

Single molecule DNA profiling. A novel AFM-based single molecule DNA profiling approach is described below: Unlike optical mapping, a single molecule restriction mapping technique for genome-sized ($10^5$-$10^7$ bp) DNA, the new approach can handle cDNA-sized (<4×$10^3$ bp) DNA molecules (18-21). In optical mapping, large DNA molecules are stretched and fixed to a glass substrate, followed by in situ restriction endonuclease digestion. No sequence-specific probes are required since restriction cleavage sites are photographed directly following fluorescent staining of the stretched DNA molecules. This method is robust and facilitated the mapping of restriction sites across the whole genomes of several microbes (20, 22). While providing an advance over conventional, pulse-field gel-based techniques, optical mapping cannot resolve restriction sites spaced closer than 800 bp, corresponding to cleavage sites roughly 264 nm apart (21).

Tapping or non-contact mode AFM has lateral resolution better than 2 nm in ambient conditions, which corresponds to 6 bp in a linear B-DNA molecule (23-25). This resolution is critical because many biologically relevant sequences, including gene promoter regions and mRNAs, are less than 6,000 bp (2,000 nm) long (17). AFM is capable of accurately sizing small DNA molecules (<$10^3$ bp) and identifying single labeling moieties. (26-37) The high precision of AFM sizing means that a useful fingerprint can be determined without the need to average results from many observations as is the case with optical single molecule sizing techniques (18-20).

Figure 1B:
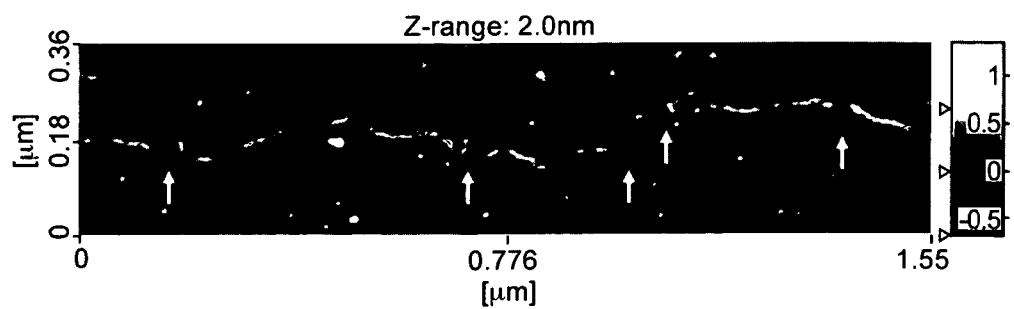

A potential alternative approach to optical mapping is AFM profiling, in which elongated DNA molecules are fixed to the surface of positively charged mica (FIG. 1A). DNA strands containing multiple recognition sites, such as RsaI, are cleaved in place with subsequent washing and drying steps displacing the cleaved ends to form observable gaps in each molecule. The distance between gaps, measured along the backbone contour, is converted to polymer chain length at 0.33 nm/bp (37) to generate a partial-sequence map of each DNA double-strand. An AFM image of a 4,700 bp plasmid, pEYFP-C1, containing five gaps from RsaI digestion is shown (FIG. 1B). The resulting cut fragments range in size from 275 to 2,000 bp (90 to 650 nm).

Surface properties. Surfaces compatible with in situ restriction digestion must bind and retain small DNA fragments (<$10^3$ bp). In addition, these surfaces must have smaller contour irregularities than the 2 nm diameter of DNA. APTES silanization generates roughness that is generally proportional to the amount of silane deposited on the surface (18). More adhesive surfaces that hold small fragments require more adsorbed aminosilane, which in turn generates greater roughness.

Figure 2:
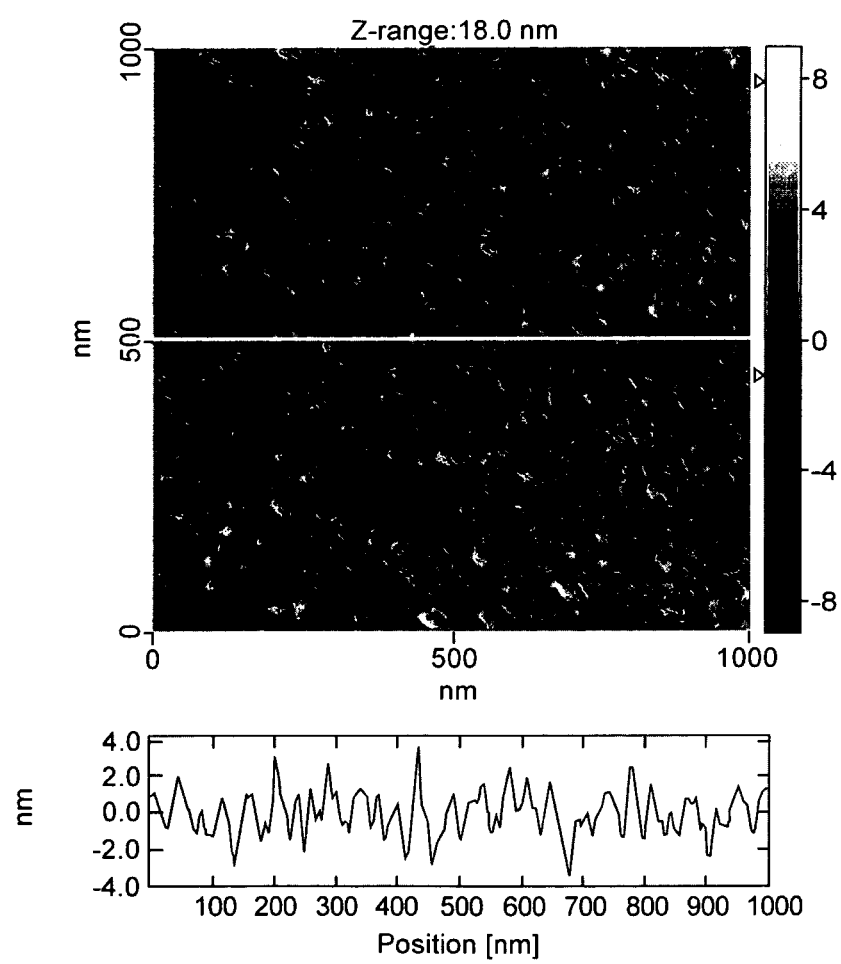
FIG. 2 depicts an atomic force microscope (AFM) image of a typical silanized glass cover slip.

Surfaces produced by silanization for optical mapping are rough (18) (FIG. 2). The contour profile shows surface height variations that range from 2 to 4 nm, with a RMS roughness of ~1.4 nm. Thus, while these surfaces are suitable for fluorescent imaging, they are too uneven for AFM imaging of DNA. Additionally, optical restriction maps that employ a thin polyacrylamide gel 'cap' over the surface-fixed DNA help retain small, loosely bound restriction fragments (22). Unfortunately, this gel cap is not suitable for AFM imaging.

Figure 3:
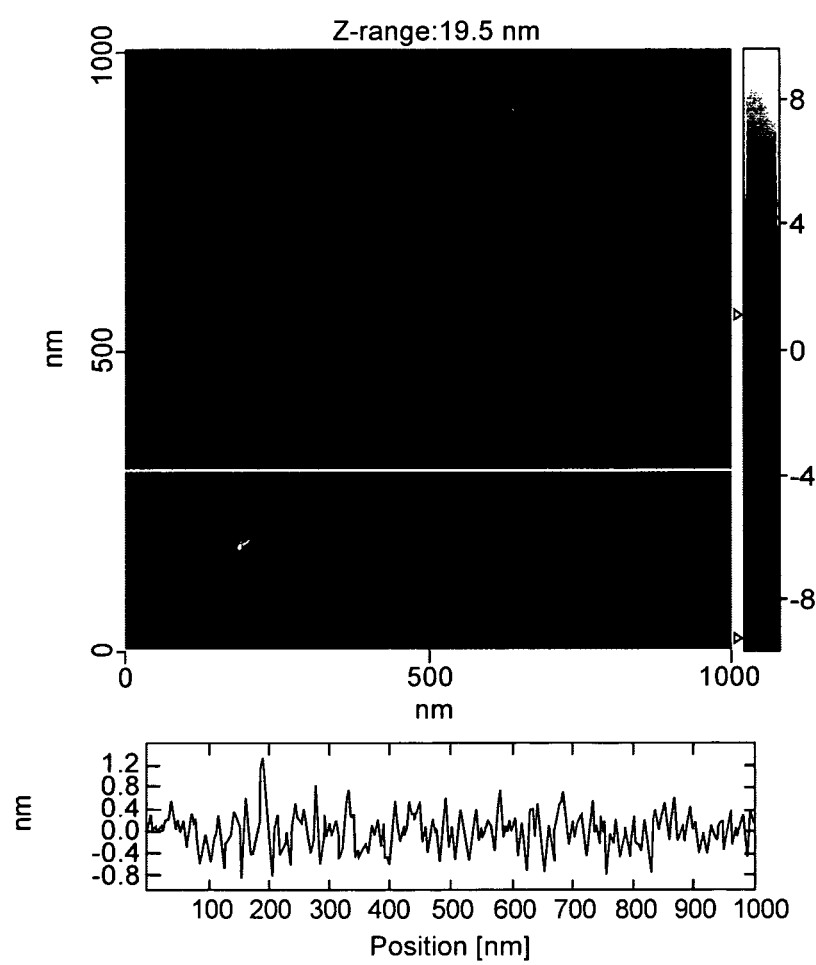
FIG. 3 depicts an AFM image of a typical silanized mica disk.

To address the surface contour problem, we developed an APTES application protocol to produce an AFM-compatible surface that retains enough positive charge to bind and hold small DNA fragments in situ (FIG. 3). The contour profile shows surface irregularities <1 nm in height and an RMS roughness of ~0.4 nm, which is smooth enough to resolve DNA molecules using AFM. There are several differences in our procedure from surface preparations used in optical restriction mapping. These include the use of mica instead of glass as a substrate, which is initially smoother (RMS roughness <0.1 nm compared to ~1 nm) and when freshly cleaved requires no precleaning (24), and a 30 m APTES exposure to aqueous solution instead of several hours (18). Silane hydrolysis and surface adsorption kinetics indicate that polymerized aggregates of multifunctional silanes accumulate in solution rapidly after 10 m in aqueous solvent, and these adsorbed aggregates increase roughness on silanized silica substrates (38-40).

In situ DNA digestion seems to increase surface roughness, resulting in a reduced contrast AFM image, although this reduction is not great enough to preclude sharp AFM imaging. One source of roughness is the restriction enzyme, which adheres to the positively charged surface, though less avidly than negatively charged DNA. Even without enzyme treatment, the contrast in AFM images is reduced after treatment with enzyme digestion buffer. The cause for increased surface roughness is unknown but may involve adsorption of salt from the restriction enzyme buffer or rearrangement of the APTES layer itself when exposed to aqueous solution.

Figure 4:
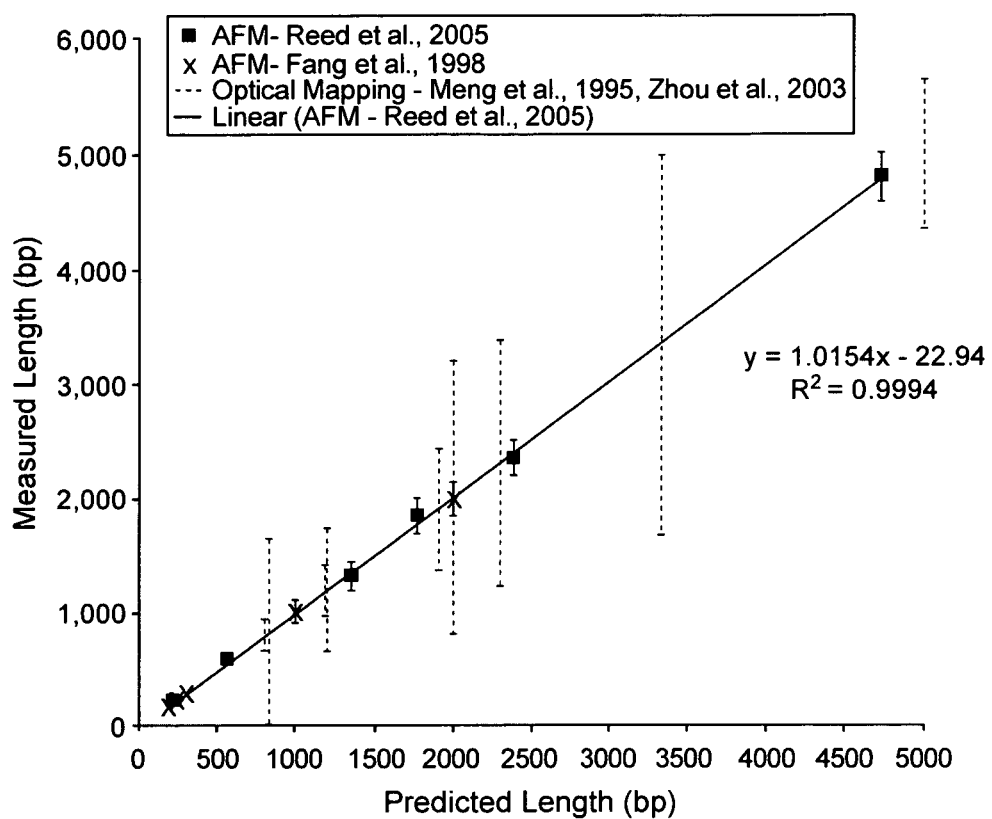
FIG. 4 depicts AFM sizing of surface fixed double-stranded DNA.

Sizing DNA with AFM. Previously, AFM was used to size small DNA fragments fixed to mica in a system similar to the one reported here (37). AFM-derived fragment contour lengths and a fixed conversion formula for chain length to bp reliably sized DNA molecules of 100 to 2,000 bp with dispersion of less than 10%. One key difference in that study from the current one is that individual molecules were deposited from solution rather than being generated as in situ fragments from larger DNA molecules. Advantages to the current method include increased surface fixation avidity and the ability to use higher ionic strength washing solutions. These differences in technique could alter the observed chain length of DNA, which is an anionic polymer. A series of six 230 to 4,731 bp DNA fragments measured using the AFM backbone contour length and a conversion of 0.33 nm/bp provided results that duplicated published data in both sizing accuracy and dispersion (19). The linear regression slope coefficient for this data was 1.0154 with an $R^2$ of 0.9994 (FIG. 4). As a reference, the data compared favorably with single DNA molecule sizing data from fluorescence-based optical mapping (20). The advantage of AFM in single fragment sizing is apparent in the lower sizing dispersion (CV generally <10% vs. >16%) and the ability to accurately size very small molecules (<$10^3$ bp). Notably, with AFM sizing a separate size standard in the sample is not required to convert backbone contour length accurately to bp. This is superior to fluorescent methods, which require internal references in each image to convert fluorescence intensity into molecular length.

Restriction map of pEYFP-C1. A restriction endonuclease cleavage map was constructed from a small number (<50) of identical 4,731 bp pEYFP-C1 plasmid molecules, to simulate fingerprinting a short genomic sequence. In practice, this type of analysis could be used to detect short sequence insertions or deletions in an intragenic region or to partially assess the methylation state of target DNAs. The starting sample was an aqueous solution of pEYFP-C1, which was linearized by digestion with either StuI or NheI. Linear pEYFP-C1 molecules of each type were then deposited on derivatized mica and in situ digested with PstI. The digested, surface-fixed molecules were imaged with AFM to determine the location of the PstI cleavage sites within each molecule.

Figure 5A:
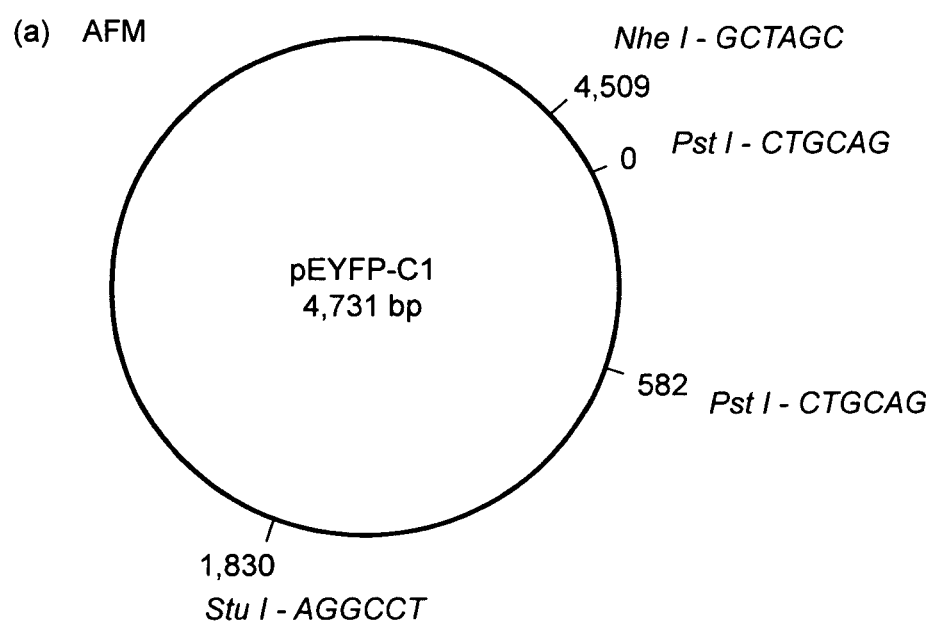
FIGS. 5A and 5B depict a composite map of endonuclease restriction recognition sequences within DNA plasmid pEY-FPC1, as determined by AFM (FIG. 5A) and as determined by actual sequence (FIG. 5B).
Figure 5B:
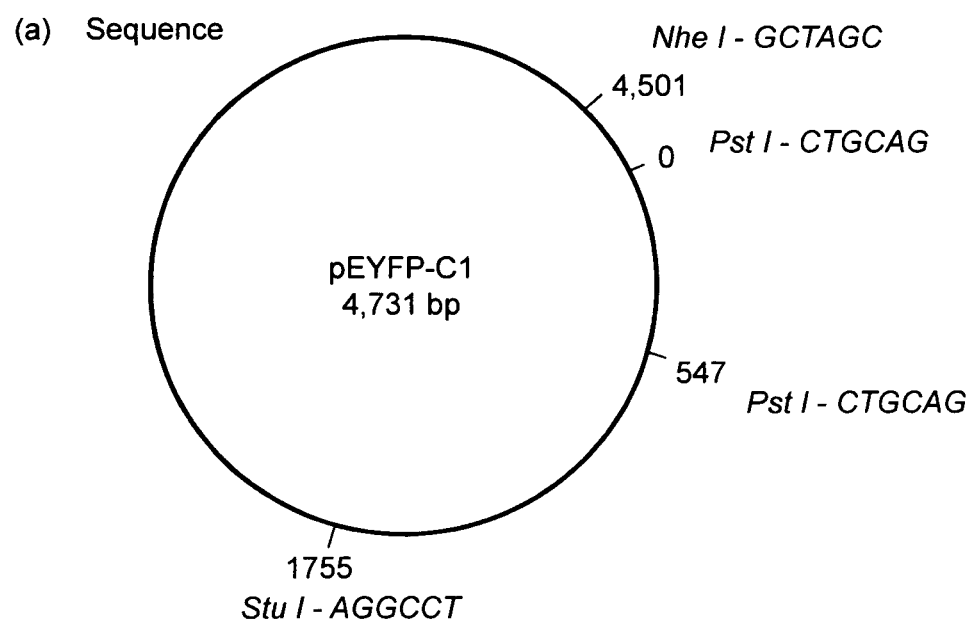

A composite cleavage site map of circular pEYFP-C1 was constructed from the StuI+PstI and NheI+PstI data (FIG. 5). Small digestion fragments were lost to variable extents during sample preparation and washing steps. As a result, many of these fragments were displaced from their proper location or completely washed from the surface. In total 10-20% of the molecules remained measurable after processing was complete. For this reason, maps were constructed from molecules that were cut once rather than twice using PstI. Fifteen 1-cut molecules were measured from each of the StuI and NheI linearized samples. The composite map thus represents pooled data from 30 individual molecules. Despite the small number of observations made, the endonuclease recognition sequences are localized with good accuracy (relative error <7%). This is consistent with the low sizing dispersion seen in single fragment sizing measurements (FIG. 4) and underscores the power of this method to construct accurate high resolution fingerprint maps from very small samples.

Profiling CD44 in a binary mixture. Next, the profile from a mixture of two low abundance cDNAs that differ slightly in sequence was performed. In principle this process could provide direct measurements of mRNA expression from multiple genes in single cells (1, 2, 10). A binary mixture was generated to contain equal concentrations of human CD44 cDNA and plasmid pOTB7, which contains a truncated isoform of the human CD44 cDNA. Normally CD44 encodes an 80-kDa, 742 amino acid cell-surface glycoprotein involved in cell-cell interactions and tumor metastasis (15). CD44 is expressed in multiple isoforms in hematopoietic, lymphoid, and epithelial tissues (41). This diversity of isoforms derives from alternative splicing of the primary RNA transcript, with more than 10 distinct splice variants identified (42). Individual isoforms may signal tumor progression and their detection in surgical biopsies has been postulated as an important biomarker for metastatic potential (15, 43). Here, a truncated splice variant (CD44v) that lacks exons 3-19 and contains the signal peptide and first two exons of the full length CD44 mRNA is used (44). Both CD44v cDNA and pOTB7 molecules are approximately 1,800 bp (594 nm) in length and contain a PstI recognition sequence 354 bp (117 nm) from their 5' ends. CD44v3 has an additional PstI site 1,046 bp (345 nm) from its 5' end (FIG. 6).

Figure 7:
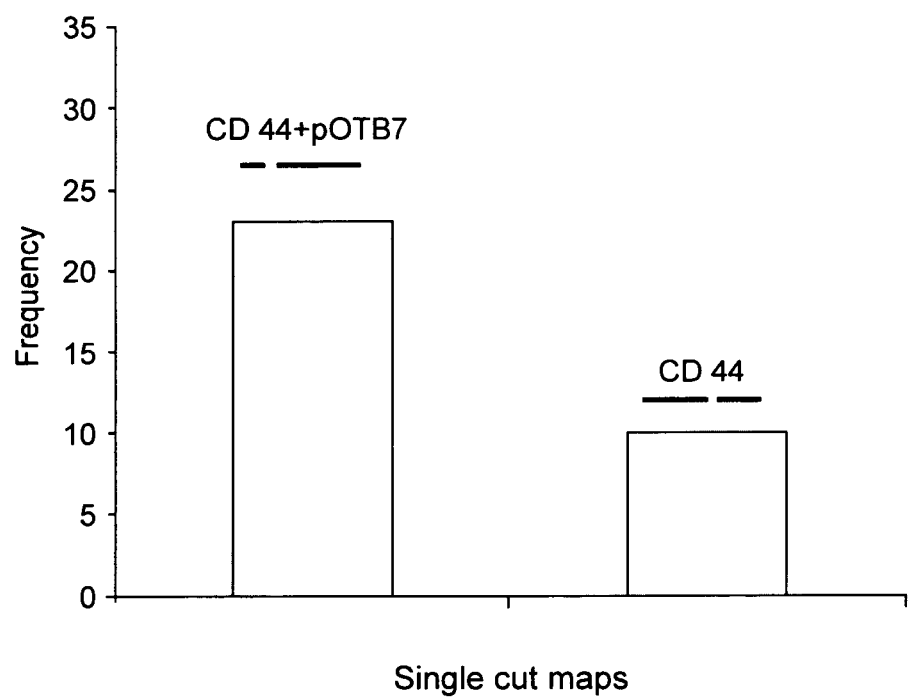
FIG. 7 depicts the frequency of molecules vs. PstI cleavage pattern determined from a 1:1 mixture of pOTB7 and CD44v DNA.
Figure 9:
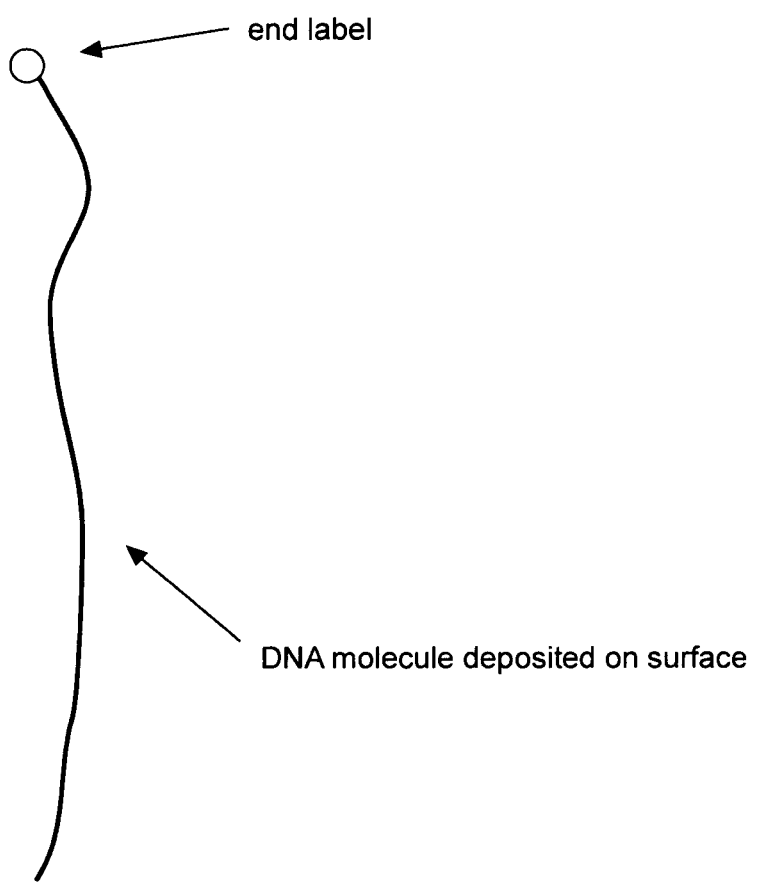
FIGS. 9-17 depict various aspects of a subject method for immobilizing a nucleic acid onto an insoluble support.
Figure 10:
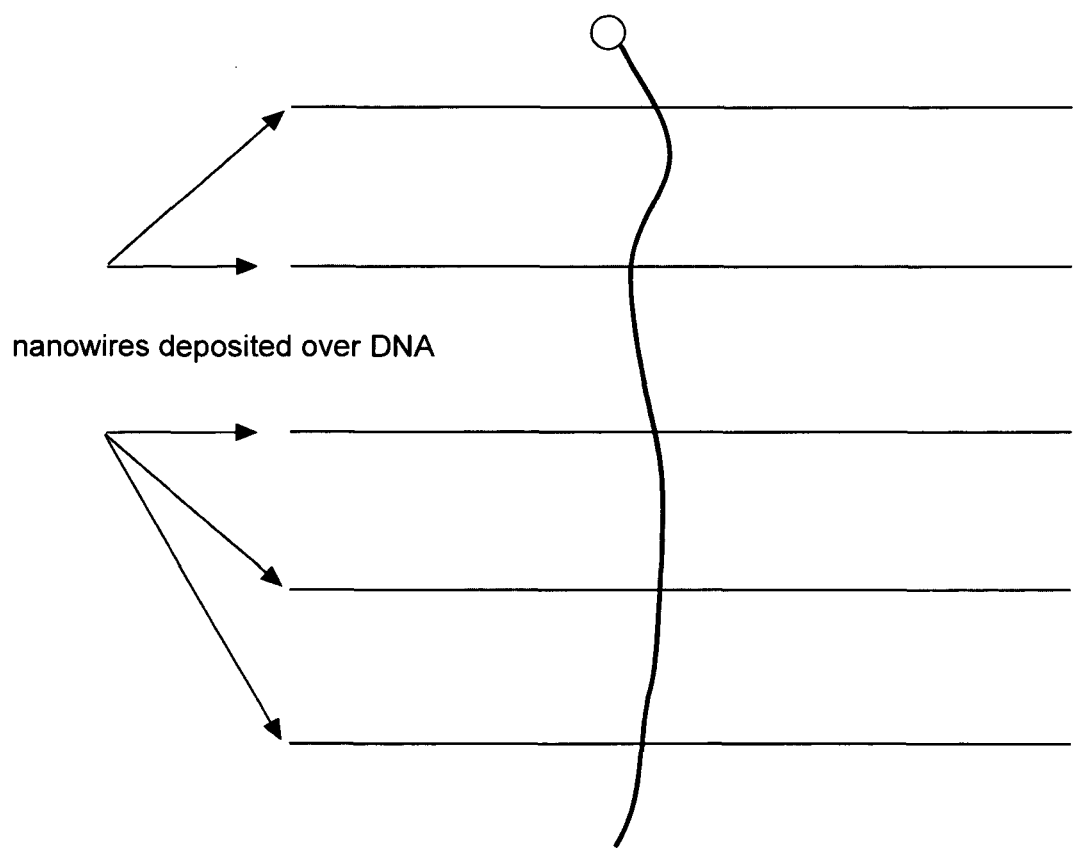
Figure 11:
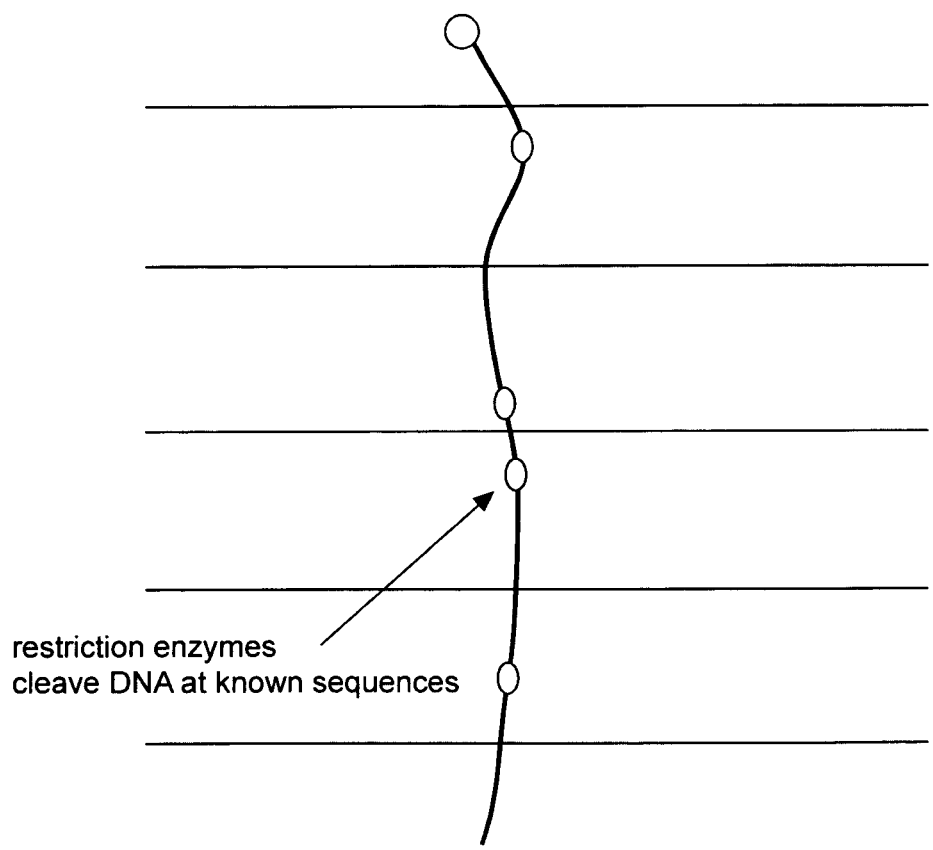
Figure 12:
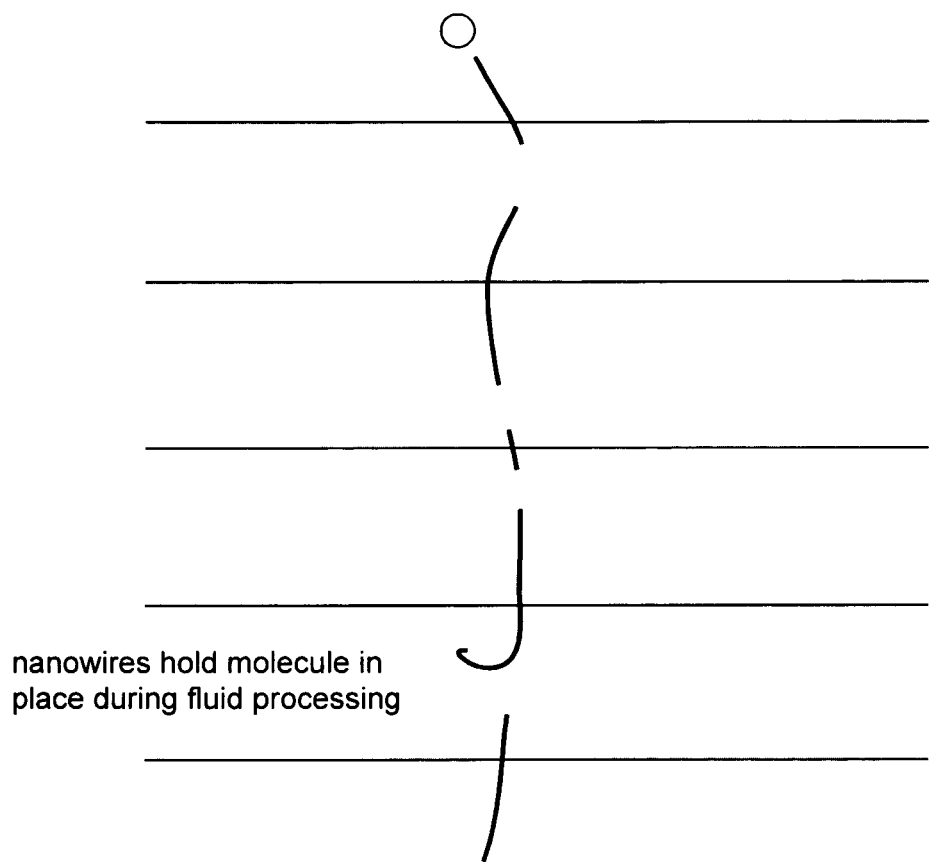
Figure 13:
Figure 14:
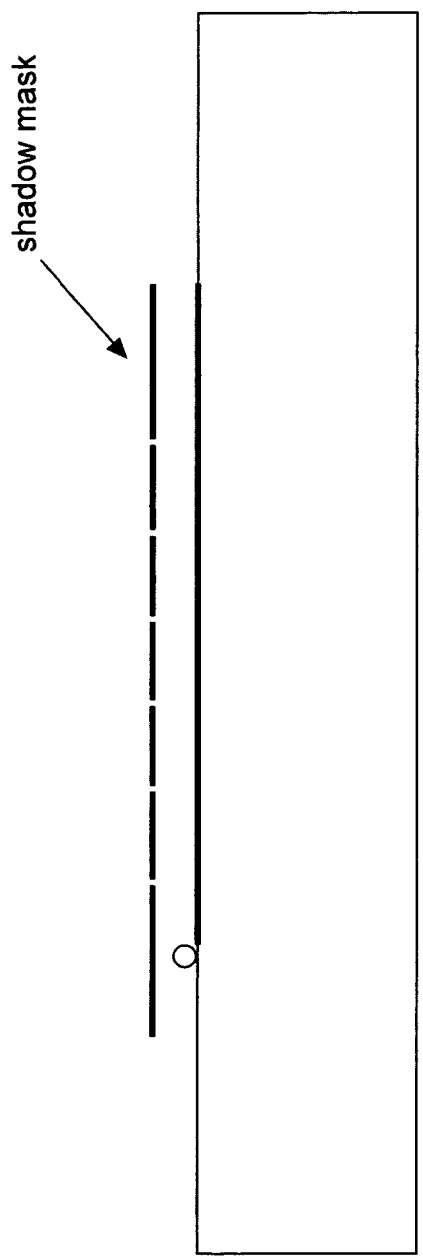
Figure 15:
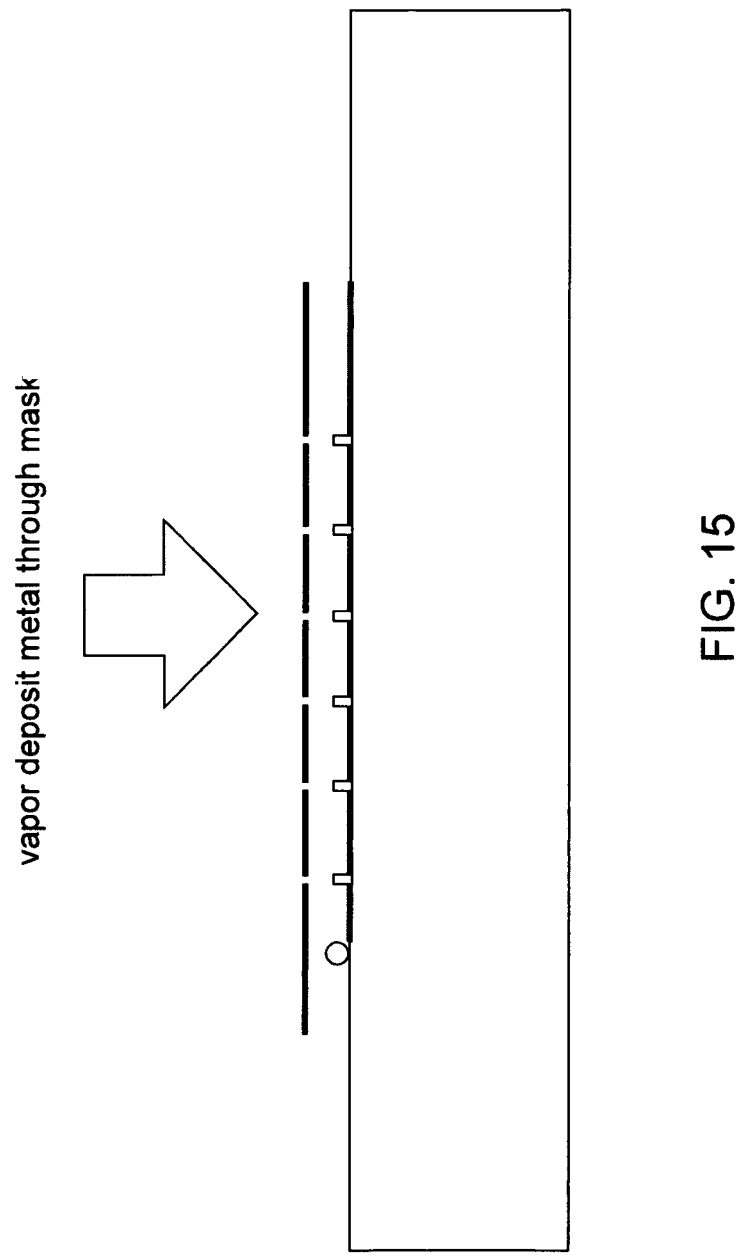
Figure 16:
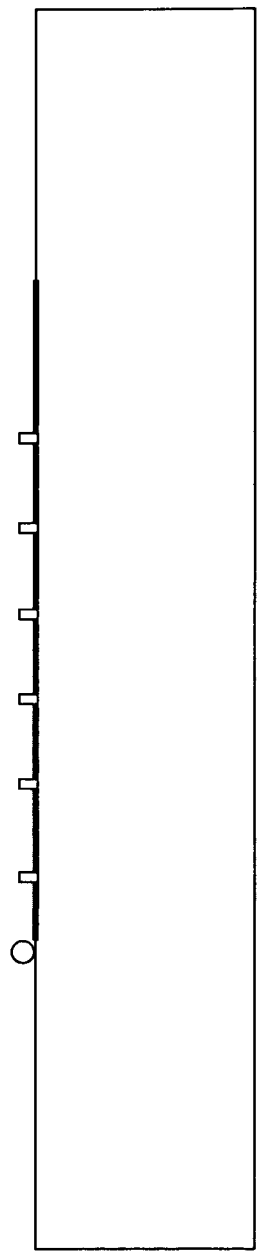
Figure 17:
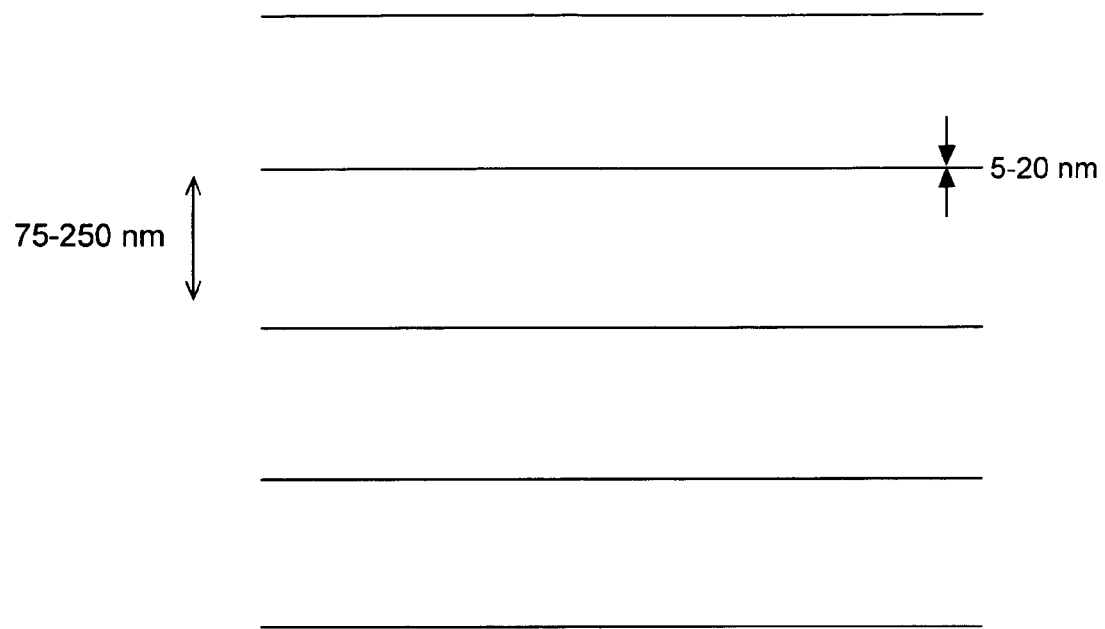
Figure 18:
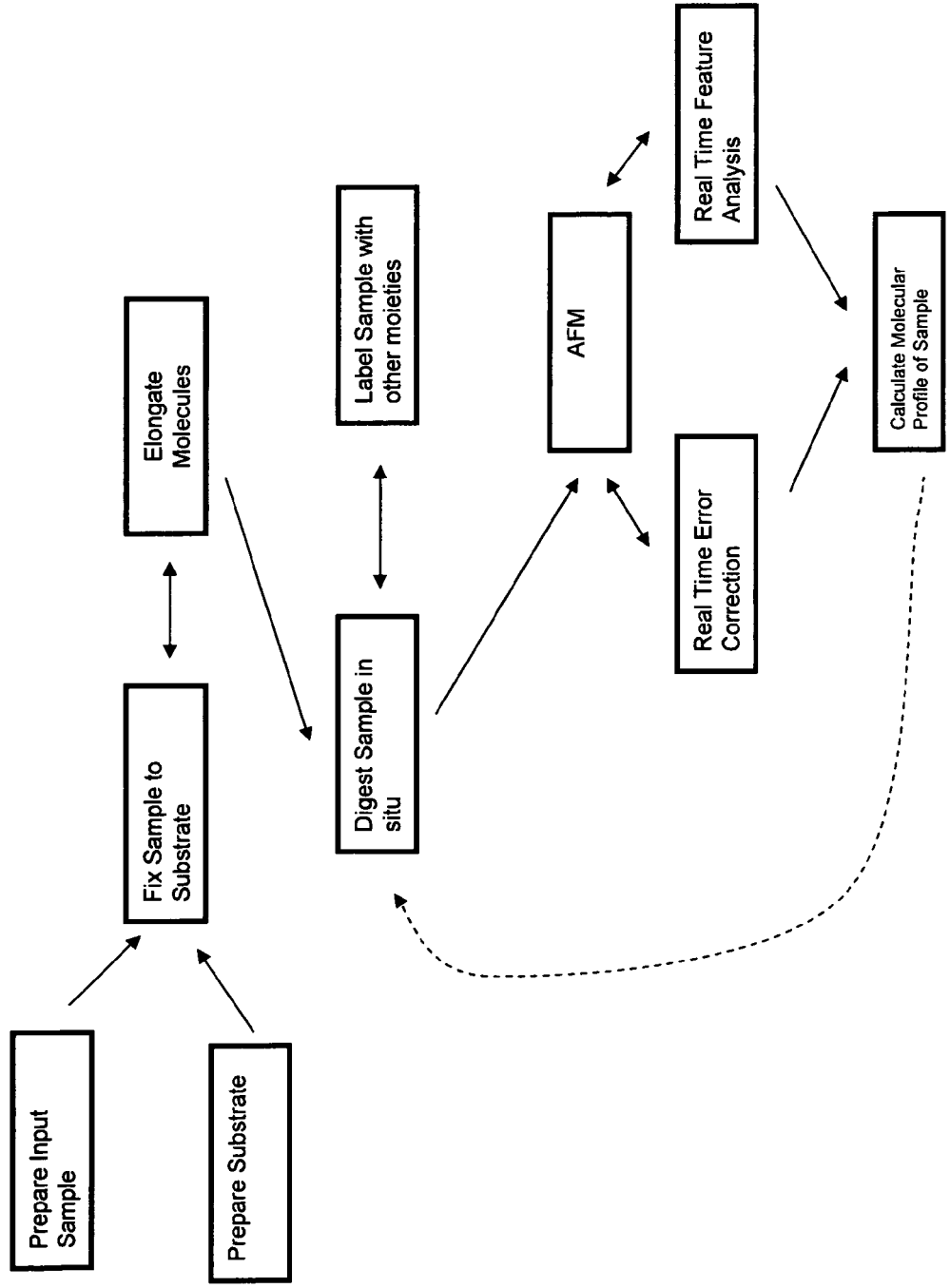
FIG. 18 is a schematic depiction of a subject method for detecting a nucleic acid analyte and assigning a profile of a feature to a nucleic acid.

Using conditions already described, an in situ digestion of a 1-1 mixture of CD44v+pOTB7 was performed, followed by and profiling of the digested sample with AFM. As for pEYFP-C1, molecules cut once with PstI rather than twice were chosen for AFM imaging to increase yield. The frequency of 1-cut maps determined from a random collection of 50 1 μm×1 μm AFM images was determined (FIG. 7). In total, the collected image set contained fewer than 500 molecules (10 per image) and of that less than 50 were measured. In the sample, molecules with a PstI cleavage ~354 bp+/−10% from one end were about 2-fold more prevalent than those with a site 1,046 bp+/−10% from an end (FIG. 7). This distribution of 1-cut maps provides the expected frequency from a 1:1 mixture of the two molecules. Therefore, an accurate determination of the relative abundance of two distinct cDNA species in a mixture using less than 50 individual molecules was obtained. This result demonstrates that this method is robust and can accurately discriminate mRNA-sized molecules in very low abundance in heterogeneous samples.

FIG. 1. Experimental scheme for single molecule DNA profiling using restriction endonucleases. (a) Endonuclease proteins bind oligomeric nucleotide recognition sequences within a surface fixed, duplex DNA molecule. The enzymes cleave the DNA strand at the recognition sites in situ, leaving small gaps (generally <100 nm) visible in the AFM image. Because the molecule remains fixed to the surface during the entire process the order and distance between the cleavage sites is retained. This serves as a partial nucleotide sequence fingerprint that can be used to identify the molecule. (b) An AFM image of a 4,700 bp DNA plasmid molecule (pEYFPC1) in situ digested with endonuclease Rsa I. Five cleavage sites visible (white arrows) as breaks in the molecule backbone correspond to the locations of the Rsa I recognition sequence 5'GATC.

FIG. 2. AFM image of a typical silanized glass cover slip prepared using a protocol from Jing et al. (19) The surface is visibly rough and the contour, indicated below, shows the features have a height of 2-4 nm.

FIG. 3. AFM image of a typical silanized mica disk used in this study for AFM imaging in situ restriction digestion. Below, the contour indicates features generally smaller than one nm.

FIG. 4. AFM sizing of surface fixed ds DNA. Mean length in base pairs for pools of six different linear DNA molecules are plotted as dark squares (n=10-40 molecules). Backbone contour length in nanometers is converted to base pairs using the nominal pitch of duplex beta DNA (0.33 nm/bp (37)). Fragments range in size from 230 to 4,731 bp (90 to 1,561 nm). Error bars represent sample standard deviation. The x-axis is the length predicted from sequence and the y-axis is the contour length as measured with AFM. A linear regression of our measurements is displayed in the figure. Our measurements are consistent with Feng et al (37) who used a similar AFM sizing method (white circles). To illustrate the relative precision of our technique we included data from a competing optical single molecule sizing method (optical mapping, broken vertical lines (18-21)).

FIG. 5. A composite map of endonuclease recognition sequences within DNA plasmid pEYFPC1, determined in bp by AFM (a) and (b) the actual location as determined by full length sequence. One PstI site is chosen as the arbitrary origin in the circular DNA molecule. The enzymes and their recognition sequences are labeled next to the tick marks outside the circle.

FIG. 6. Using the single molecule profiling technique we measured the relative abundance of pOTB7 and CD44 cDNA in a sample containing less than 500 molecules. Undigested the two species appear identical in an AFM image. By in situ digestion with endonuclease Pst I we can identify each molecule by the pattern of breaks in its backbone corresponding to the enzyme recognition sequence.

FIG. 7. Frequency of molecules vs. Pst I cleavage pattern determined from a 1-1 mixture of pOTB7+CD44v DNA. Molecules with a pattern common to both pOTB7 and CD44v were twice as prevalent as those with a pattern unique to CD44v.

FIG. 8. Schematic of single molecule profiling. (a) image of cDNA molecules with backbone breaks corresponding to restriction sites. Some molecules are incompletely digested. (b) digital representation of molecules where '1' bit represents a cut and '0' represents no cut. (b) grouping digital patterns two identify, in this case, two distinct species.

Example 2

Anchoring Nucleic Acids to an Insoluble Support

FIGS. 9-17 depict a method for immobilizing a nucleic acid onto the surface of an insoluble support.

A shadow mask is produced by milling slots or holes in a thin silicon nitride membrane (<1 micron thick). These slots or holes have the approximate dimensions of the features to be vapor deposited.

Nucleic acid molecules are elongated and deposited on an appropriate flat, non-soluble substrate. This substrate may or may not be derivatized, e.g., with APTES, etc.

Material is vapor deposited on the substrate through the shadow mask using a controlled method such as e-beam evaporation of the metal in vacuum. The shadow mask may be tilted with respect to the substrate surface so that effective aperture is thinner and thus the deposited features are smaller. The shadow mask may be moved slowly as the material is deposited so as to 'write' various features.

The features deposited on the substrate through the shadow mask act to physically hold the nucleic acids on the surface when the substrate is exposed to liquid.

A variation of this technique involves use of other materials, such as a silane compound, or a functionalized alkane, or any other sublimable chemical in place of metal.

Example 3

In principle, high-resolution single molecule ordered restriction mapping provides an alternative approach to gene expression profiling, since a large number of cDNAs can be accurately clustered into species with similar maps and their cluster sizes directly estimated. For this purpose, the patterns of restriction sites in each cDNA molecule must provide a species-specific fingerprint or signature and two distinct species must be distinguishable by their signatures. These requirements are readily achieved in most ideal situations where each species differs from any other in their sequence composition, the mapping technology approaches single-base-pair resolution, and restriction enzymes almost always cleave with high fidelity and efficiency.

In reality, both mapping resolution and restriction enzyme digestion efficiency deviate from the ideal, but without seriously affecting the feasibility of this approach, as demonstrated with the following estimates of species resolution. A restriction map can be represented as a digital binary signature, (e.g., 00100110), in which each break point is noted by a non-zero bit, and the length of a fragment between two neighboring breaks by the number of intervening consecutive zero-bits. The length in bits is an integer number, measuring distances originally in bp, and determined by the precision with which one can measure the distance between two restriction sites. This, in turn, is a function of the imaging resolution and the conversion factor used to calculate length in bp from molecular dimensions. As the resolution worsens, the signatures become shorter, and as the restriction digestion rate drops, the corrupted mapped signature deviates from the true signature. In each case, our ability to disambiguate pairs of cDNAs belonging to different species becomes progressively impaired. In order to understand the effect of these sources of unavoidable errors and engineer an optimal technology, the following probabilistic analysis is helpful. This analysis relies on a few simplifying assumptions: all cDNAs are of the same length, L=2 kb, and the achievable resolution (called '$\alpha$') varies from 10 to 24 bp, or 3 to 8 nm using the pitch of B-DNA as the conversion factor. Two kb is a reasonable assumption for average cDNA length derived from mRNA of mammalian cells (17). Also, recalculation of this analysis for a range of 1.5 to 2.5 kb produced equivalent results.

Initially, consider a sample calculation that assumes a resolution $\alpha$=10 bp. The 2 kb molecule is divided up into 200 bins of width 10 bp, thus the signatures are of length M=200 bits. At this value of M, there are an enormous number of possible signatures: $2^M \approx 1.61 \times 10^{60}$. In actuality, a mammalian cDNA sample would contain a very small subset of these possibilities, on the order of 30,000 different species. Thus, the 'real' signatures belonging to cDNA molecules can be considered as elements distributed randomly within this very large group of 'unused' possible signatures. Conceptually, with this many 'unused' signatures the chance of mistaking one 'real' signature for another 'real' signature, assuming a small number of bits change from 0 to 1 or vice versa, is practically null. Viewed another way, many bits would have to change in the corrupted signature before finding the next closest 'real' signature. The number of bits needed to change one signature to another can be thought of as a distance, called a Hamming distance. We can see that the chances of confusing two 'real' signatures, fixed at 30,000 species, increases as the number of 'unused' signatures decreases. Put another way, as we reduce the number of 'unused' signatures the Hamming distance between any two 'real' signatures shortens. The number of 'unused' signatures is a function of the number of bits in the signature, which in turn is a function of the mapping resolution. Thus, as expected, as the mapping resolution decreases the chances of mistaking one cDNA signature for another increases.

These probabilities can be calculated numerically as follows: Assume that the cDNAs monitored belong to only a small number S≈30,000 possible species, and are characterized by signatures uniformly randomly selected from all possible signatures, with a probability $\pi = |S|/2^M \approx 2.0 \times 10^{-56}$. As discussed earlier, the measured distance between a pair of signatures is the Hamming distance, or the number of bits where the signatures have differing binary values. In this case every pair of signatures in S has a Hamming distance in excess of 43 bits (with a probability $>1-10^{-12}$). The computation of this probability proceeds as follows: Start with a selected signature $f_0$ from the set S, and compute all the possible signatures whose Hamming distances from $f_0$ range between 1 and 21; there are $4.1 \times 10^{43}$ [vol=Sum[Binomial[M, k], {k, 1, MaxD−1}], MaxD=43] such signatures, and with high probability, they do not contain even a single signature from the set S [probability $>(1-10^{-2})>(1-\pi)^{vol}$]. Hence, the nearest neighbor of $f_0$ in the set S must be 43 bits or farther away.

Now let us address the issue of incomplete digestion. In this case some of the '1' bits in the signature would become '0' bits because the restriction site corresponding to that bin would not be cleaved. Note that a four cutter enzyme cleaves at any site in a random cDNA sequence with a probability $p_c=4^{-4}=1/256$, thus assigning it a signature with about $L\,p_c=8$ non-zero bits on the average. So the average 2 Kb molecule would have eight cuts and the average distance between cuts would be 256 bp. Thus intuitively speaking, no matter how low the digestion rate is, it is improbable that a 'real' digital signature can lose a large number of unit bits to become confused with another unrelated "real" signature, since each loss of unit bit only increases the Hamming distance by one in the mapped signature, without ever letting it get close to another signature in S, 43 bits or farther away. However, since the number of unit bits in the signature has a Binomial distribution with its value ranging between [0, 200], one also needs to consider the atypical situations.

Assume that the mapping resolution remains $\alpha=10$ bp and digestion rate is $p_d>0.25$ (i.e., in the worst case, only about 25% of the restriction site is digested); we then need to compute the probability that the true signature can be inferred from the mapped signature unambiguously. Conceptually we need show that even converting ¾ or fewer of the '1' bits to '0' bits results in a signature that is 'close enough' to the correct 'real' signature so that it is not confused with another 'real' signature. In this case the probability of correctly identifying the signature would be close to one. We compute this probability as follows: we let 'b' range over [0, Floor[MaxD/2]] and 'a' range over [0, M−b], we sum the probabilities that starting with a signature with (a+b) unit bits, exactly b unit bits are lost from the mapped signature as a consequence of incomplete digestion. That is, we compute Sum[Sum[Multinomial[a,b,M−a−b]$(\alpha p_c p_d)$^a$(\alpha p_c(1-p_d))$^b$(1-\alpha p_c)$^(M−a−b), {a,0,M−b}],{b,0, Floor[MaxD/2]}]]. For our example, this probability is computed to be $>1-1.4\times10^{-7}$, which is indeed very close to unity. FIGS. 8A-C show a schematic of process of clustering 'similar' digital signatures into groups associated with one 'real' cDNA signature.

Few more similar computations also show that as the resolution degrades from $\alpha=10$ bp to $\alpha=12$ bp (4 nm), then in order to achieve comparable probabilistic guarantees for unambiguous detection of about 30,000 cDNAs, we must aim for a partial digestion rate in excess of $p_d>0.5$. Further degrading the resolution to $\alpha=16$ bp/5 nm (or $\alpha=24$ bp/8 nm), a similar reasoning shows that one will need $p_d>0.85$ (or $p_d>0.995$, respectively), a rather difficult-to-achieve situation.

REFERENCES

1. Peixoto, A., Monteiro, M., Rocha, B. & Veiga-Fernandes, H. (2004) *Genome Research* 14, 1938-1947.
2. Kawasaki, E. S. (2004) in *Applications of Bioinformatics in Cancer Detection* (NEW YORK ACAD SCIENCES, New York), Vol. 1020, pp. 92-100.
3. Bashiardes, S. & Lovett, M. (2001) *Current Opinion in Chemical Biology* 5, 15-20.
4. Shih, I. M. & Wang, T. L. (2005) *Current Opinion in Oncology* 17, 33-38.
5. Blais, A. & Dynlacht, B. D. (2005) *Genes & Development* 19, 1499-1511.
6. Pahl, A. (2005) *Expert Review of Molecular Diagnostics* 5, 43-52.
7. Ewis, A. A., Zhelev, Z., Bakalova, R., Fukuoka, S., Shinohara, Y., Ishikawa, M. & Baba, Y. (2005) *Expert Review of Molecular Diagnostics* 5, 315-328.
8. Clarke, P. A., te Poele, R. & Workman, P. (2004) *European Journal of Cancer* 40, 2560-2591.
9. Evans, S. J., Watson, S. J. & Akil, H. (2003) *Integrative and Comparative Biology* 43, 780-785.
10. Camacho, A., Korn, K., Damond, M., Cajot, J. F., Litborn, E., Liao, B. H., Thyberg, P., Winter, H., Honegger, A., Gardellin, P. & Rigler, R. (2004) *Journal of Biotechnology* 107, 107-114.
11. Zhu, J., Shendure, J., Mitra, R. D. & Church, G. M. (2003) *Science* 301, 836-838.
12. Todd, R. & Margolin, D. H. (2002) *Trends in Molecular Medicine* 8, 254-257.
13. Markoulatos, P., Siafakas, N. & Moncany, M. (2002) *Journal of Clinical Laboratory Analysis* 16, 47-51.
14. Cossman, J., Annunziata, C. M., Barash, S., Staudt, L., Dillon, P., He, W. W., Ricciardi-Castagnoli, P., Rosen, C. A. & Carter, K. C. (1999) *Blood* 94, 411-416.
15. Brinkman, B. M. N. (2004) *Clinical Biochemistry* 37, 584-594.
16. French, S. W., Dawson, D. W., Miner, M. D., Doerr, J. R., Malone, C. S., Wall, R. & Teitell, M. A. (2002) *Clinical Immunology* 103, 217-230.
17. Lewin, B. (1999) *Genes VII* (Oxford University Press.
18. Reed, J., Singer, E., Kresbach, G. & Schwartz, D. C. (1998) *Analytical Biochemistry* 259, 80-88.
19. Jing, J. P., Reed, J., Huang, J., Hu, X. H., Clarke, V., Edington, J., Housman, D., Anantharaman, T. S., Huff, E. J., Mishra, B., Porter, B., Shenker, A., Wolfson, E., Hiort, C., Kantor, R., Aston, C. & Schwartz, D. C. (1998) *Proceedings of the National Academy of Sciences of the United States of America* 95, 8046-8051.
20. Zhou, S. G., Deng, W., Anantharaman, T. S., Lim, A., Dimalanta, E. T., Wang, J., Wu, T., Chunhong, T., Creighton, R., Kile, A., Kvikstad, E., Bechner, M., Yen, G., Garic-Stankovic, A., Severin, J., Forrest, D., Runnheim, R., Churas, C., Lamers, C., Perna, N. T., Burland, V., Blattner, F. R., Mishra, B. & Schwartz, D. C. (2002) *Applied and Environmental Microbiology* 68, 6321-6331.
21. Meng, X., Benson, K., Chada, K., Huff, E. J. & Schwartz, D. C. (1995) *Nature Genetics* 9, 432-438.
22. Lim, A., Dimalanta, E. T., Potamousis, K. D., Yen, G., Apodoca, J., Tao, C. H., Lin, J. Y., Qi, R., Skiadas, J., Ramanathan, A., Perna, N. T., Plunkett, G., Burland, V., Mau, B., Hackett, J., Blattner, F. R., Anantharaman, T. S., Mishra, B. & Schwartz, D. C. (2001) *Genome Research* 11, 1584-1593.
23. Klinov, D. & Magonov, S. (2004) *Applied Physics Letters* 84, 2697-2699.
24. Hansma, H. G. (2001) *Annual Review of Physical Chemistry* 52, 71-92.
25. Muller, D. J. & Engel, A. (2002) in *Atomic Force Microscopy in Cell Biology* (ACADEMIC PRESS INC, San Diego), Vol. 68, pp. 257-299.
26. Nakamura, T., Maeda, Y., Oka, T., Tabata, H., Futai, M. & Kawai, T. (1999) *Journal of Vacuum Science & Technology B* 17, 288-293.
27. Allison, D. P., Kerper, P. S., Doktycz, M. J., Spain, J. A., Modrich, P., Larimer, F. W., Thundat, T. & Warmack, R. J. (1996) *Proceedings of the National Academy of Sciences of the United States of America* 93, 8826-8829.
28. Woolley, A. T., Guillemette, C., Cheung, C. L., Housman, D. E. & Lieber, C. M. (2000) *Nature Biotechnology* 18, 760-763.

29. Hoyt, P. R., Doktycz, M. J., Modrich, P., Warmack, R. J. & Allison, D. P. (2000) *Ultramicroscopy* 82, 237-244.
30. Potaman, V. N., Oussatcheva, E. A., Lyubchenko, Y. L., Shlyakhtenko, L. S., Bidichandani, S. I., Ashizawa, T. & Sinden, R. R. (2004) *Nucleic Acids Research* 32, 1224-1231.
31. Allison, D. P., Kerper, P. S., Doktycz, M. J., Thundat, T., Modrich, P., Larimer, F. W., Johnson, D. K., Hoyt, P. R., Mucenski, M. L. & Warmack, R. J. (1997) *Genomics* 41, 379-384.
32. Hori, K., Takahashi, T. & Okada, T. (1998) *European Biophysics Journal with Biophysics Letters* 27, 63-68.
33. Sun, H. B. & Yokota, H. (2000) *Analytical Chemistry* 72, 3138-3141.
34. Seong, G. H., Niimi, T., Yanagida, Y., Kobatake, E. & Aizawa, M. (2000) *Analytical Chemistry* 72, 1288-1293.
35. Kim, J., Hirose, T., Sugiyama, S., Ohtani, T. & Muramatsu, H. (2004) *Nano Letters* 4, 2091-2097.
36. Berge, T., Ellis, D. J., Dryden, D. T. F., Edwardson, J. M. & Henderson, R. M. (2000) *Biophysical Journal* 79, 479-484.
37. Fang, Y., Spisz, T. S., Wiltshire, T., D'Costa, N. P., Bankman, I. N., Reeves, R. H. & Hoh, J. H. (1998) *Analytical Chemistry* 70, 2123-2129.
38. Bunker, B. C., Carpick, R. W., Assink, R. A., Thomas, M. L., Hankins, M. G., Voigt, J. A., Sipola, D., de Boer, M. P. & Gulley, G. L. (2000) *Langmuir* 16, 7742-7751.
39. Schwartz, D. K. (2001) *Annual Review of Physical Chemistry* 52, 107-137.
40. Zhang, F. X. & Srinivasan, M. P. (2004) *Langmuir* 20, 2309-2314.
41. Jackson, D. G., Screaton, G. R., Bell, M. V. & Bell, J. I. (1993) *Lancet* 341, 252-252.
42. Stamenkovic, I., Amiot, M., Pesando, J. M. & Seed, B. (1989) *Cell* 56, 1057-1062.
43. Matsumura, Y. & Tarin, D. (1992) *Lancet* 340, 1053-1058.
44. Bell, M. V., Screaton, G. R., Jackson, D. G. & Bell, J. I. (1993) *Journal of Cellular Biochemistry*, 332-332.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of analyzing a single double-stranded nucleic acid in a sample, the method comprising:
   immobilizing nucleic acids on an insoluble support in a substantially elongated configuration;
   subjecting the immobilized nucleic acids to restriction endonuclease digestion, thereby creating gaps along the backbone of each double stranded nucleic acid; and
   measuring the distance between the gaps along the backbone of a single nucleic acid using scanning probe microscopy, thereby obtaining a restriction profile for the nucleic acid.
2. The method of claim 1, wherein the scanning probe microscopy is atomic force microscopy (AFM).
3. The method of claim 1, wherein the insoluble support retains nucleic acids at least about 10 base pairs in length.
4. The method of claim 1, wherein the nucleic acids are modified with a methylation agent prior to restriction endonuclease digestion.
5. The method of claim 1, wherein the nucleic acids have a length of from about 500 nucleotides to about 5000 nucleotides.
6. The method of claim 1, wherein the nucleic acid is present in an abundance of from about 1 nucleic acid molecule per $10^2$ nucleic acid molecules to about 1 nucleic acid molecule per $10^6$ nucleic acid molecules.
7. The method of claim 1, wherein the sample comprises from about $10^2$ to about $10^8$ distinct nucleic acids.
8. The method of claim 1, wherein said insoluble support is planar.
9. The method of claim 1, further comprising comparing the obtained restriction profile with a known restriction profile of a reference nucleic acid.
10. The method of claim 2, wherein the AFM is programmed to scan the surface of the insoluble support at a higher speed than the speed used to scan the modified immobilized nucleic acids.
11. The method of claim 2, wherein the AFM is programmed to obtain two or more cross-sectional profile data points per unit length of modified immobilized nucleic acid, wherein the unit length is at least about 2 nanometers, wherein at least one of the data points is taken from a cross-sectional peak of the modified immobilized nucleic acid.
12. The method of claim 1, further comprising comparing two obtained restriction profiles with one another.
13. The method of claim 1, further comprising comparing three or more restriction profiles with one another.
14. The method of claim 1, wherein the restriction profile is a binary digital profile.

* * * * *

UNITED STATES PATENT AND TRADEMARK OFFICE
CERTIFICATE OF CORRECTION

| | | |
|---|---|---|
| PATENT NO. | : 8,566,038 B2 | Page 1 of 1 |
| APPLICATION NO. | : 11/582938 | |
| DATED | : October 22, 2013 | |
| INVENTOR(S) | : James K. Gimzewski | |

It is certified that error appears in the above-identified patent and that said Letters Patent is hereby corrected as shown below:

In the Specification

Column 1, line 13 should read as follows:

Statement Regarding Federally Sponsored Research

--This invention was made with Government support under Grant No. HG003714, awarded by the National Institutes of Health. The Government has certain rights in the invention.--

Signed and Sealed this
Nineteenth Day of August, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,566,038 B2 | Page 1 of 1 |
| APPLICATION NO. | : 11/582938 | |
| DATED | : October 22, 2013 | |
| INVENTOR(S) | : James K. Gimzewski et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1545 days.

Signed and Sealed this
Twenty-eighth Day of April, 2015

Michelle K. Lee
*Director of the United States Patent and Trademark Office*